(12) United States Patent
Kusumoto

(10) Patent No.: US 11,007,016 B2
(45) Date of Patent: May 18, 2021

(54) INTRACARDIAC ULTRASOUND CATHETER HANDHELD ADAPTER

(71) Applicant: Walter Kusumoto, Chico, CA (US)

(72) Inventor: Walter Kusumoto, Chico, CA (US)

(*) Notice: Subject to any disclaimer, the term of this patent is extended or adjusted under 35 U.S.C. 154(b) by 253 days.

(21) Appl. No.: 16/282,835

(22) Filed: Feb. 22, 2019

(65) Prior Publication Data

US 2019/0183588 A1 Jun. 20, 2019

Related U.S. Application Data

(63) Continuation-in-part of application No. 15/713,307, filed on Sep. 22, 2017.

(Continued)

(51) Int. Cl.
*A61B 34/20* (2016.01)
*A61B 8/12* (2006.01)
(Continued)

(52) U.S. Cl.
CPC ............ *A61B 34/20* (2016.02); *A61B 8/0883* (2013.01); *A61B 8/12* (2013.01); *A61B 8/14* (2013.01); *A61B 8/4254* (2013.01); *A61B 8/445* (2013.01); *A61B 8/463* (2013.01); *A61B 18/1477* (2013.01); *A61B 18/1492* (2013.01); *A61B 2017/00053* (2013.01); *A61B 2017/00243* (2013.01); *A61B 2018/00172* (2013.01); *A61B 2018/00178* (2013.01);
(Continued)

(58) Field of Classification Search
CPC ......... A61B 34/20; A61B 8/0883; A61B 8/12; A61B 8/14; A61B 8/4254; A61B 8/445; A61B 8/463; A61B 18/1477; A61B 18/1492; A61B 2034/2051; A61B 2034/2053; A61B 2034/2063; A61B 2090/3784; A61B 2017/00053; A61B 2017/00243; A61B 2018/00172; A61B 2018/00178; A61B 2018/00351; A61B 2018/00577; A61B 2018/00839; A61B 2018/00982
USPC ....................................... 600/508
See application file for complete search history.

(56) References Cited

U.S. PATENT DOCUMENTS 5,405,376 A 4/1995 Mulier
6,165,164 A 12/2000 Hill
(Continued)

*Primary Examiner* — Aaron F Roane
(74) *Attorney, Agent, or Firm* — Heisler & Associates

(57) ABSTRACT

An intracardiac ultrasound catheter or other intravascular imaging tool is provided with an adapter to allow the imaging tool to be used both subcutaneously and supracutaneously, and especially at different stages of a single intravascular procedure. The adapter covers a tip of the imaging tool and preferably includes an echogenic window to facilitate gathering of ultrasound images through this window in the adapter. With the adapter in place, the intracardiac ultrasound can be used supracutaneously, such as at a femoral artery/vein location for imaging to improve vascular access, such as with an appropriate percutaneous needle. The adapter is then removed and the same imaging tool can be inserted percutaneously and intravascularly for use, such as in intracardiac imaging accompanying and intracardiac procedure. The intracardiac ultrasound probe is preferably coupled to an electrophysiology mapping system both when used supracutaneously and when used intravascularly.

11 Claims, 12 Drawing Sheets

Related U.S. Application Data

(60) Provisional application No. 62/633,793, filed on Feb. 22, 2018, provisional application No. 62/398,394, filed on Sep. 22, 2016, provisional application No. 62/516,556, filed on Jun. 7, 2017.

(51) Int. Cl.
| | | |
|---|---|---|
| *A61B 8/00* | (2006.01) | |
| *A61B 8/14* | (2006.01) | |
| *A61B 18/14* | (2006.01) | |
| *A61B 8/08* | (2006.01) | |
| *A61B 18/00* | (2006.01) | |
| *A61B 90/00* | (2016.01) | |
| *A61B 17/00* | (2006.01) | |

(52) U.S. Cl.
CPC ............. *A61B 2018/00351* (2013.01); *A61B 2018/00577* (2013.01); *A61B 2018/00839* (2013.01); *A61B 2018/00982* (2013.01); *A61B 2034/2051* (2016.02); *A61B 2034/2053* (2016.02); *A61B 2034/2063* (2016.02); *A61B 2090/3784* (2016.02)

(56) References Cited

U.S. PATENT DOCUMENTS

| | | |
|---|---|---|
| 6,171,303 B1 | 1/2001 | Ben-Haim |
| 6,206,874 B1 | 3/2001 | Ubby |
| 6,319,375 B1 | 11/2001 | Plicchi |
| 6,496,712 B1 | 12/2002 | Dahl |
| 7,815,577 B2 | 10/2010 | Krishnan |
| 7,917,216 B1 | 3/2011 | Ryu |
| 8,010,186 B1 | 8/2011 | Ryu |
| 8,050,739 B2 | 11/2011 | Eck |
| 8,172,757 B2 | 5/2012 | Jaffe |
| 8,285,364 B2 | 10/2012 | Barbagli |
| 8,287,531 B2 | 10/2012 | Mest |
| 8,326,419 B2 | 12/2012 | Rosenberg |
| 8,388,549 B2 | 3/2013 | Paul |
| 8,403,925 B2 | 3/2013 | Miller |
| 8,406,866 B2 | 3/2013 | Deno |
| 8,755,864 B2 | 6/2014 | Hauck |
| 8,825,144 B2 | 9/2014 | Starks |
| 2006/0253032 A1 | 11/2006 | Altmann |
| 2007/0021648 A1 | 1/2007 | Lenker |
| 2008/0177138 A1 | 7/2008 | Courtney |
| 2008/0183072 A1 | 7/2008 | Robertson |
| 2009/0171196 A1 | 7/2009 | Olson |
| 2011/0087105 A1 | 4/2011 | Ridley |
| 2011/0087175 A1 | 4/2011 | Krishnan |
| 2011/0098564 A1 | 4/2011 | Larson |
| 2012/0172717 A1 | 7/2012 | Gonda |
| 2013/0241929 A1 | 9/2013 | Massarwa |
| 2014/0148688 A1 | 5/2014 | Ludwin et al. |
| 2014/0257102 A1 | 9/2014 | Hossack |
| 2014/0350401 A1* | 11/2014 | Sinelnikov ......... A61B 17/2202 600/439 |
| 2015/0289781 A1 | 10/2015 | Grunwald |

* cited by examiner

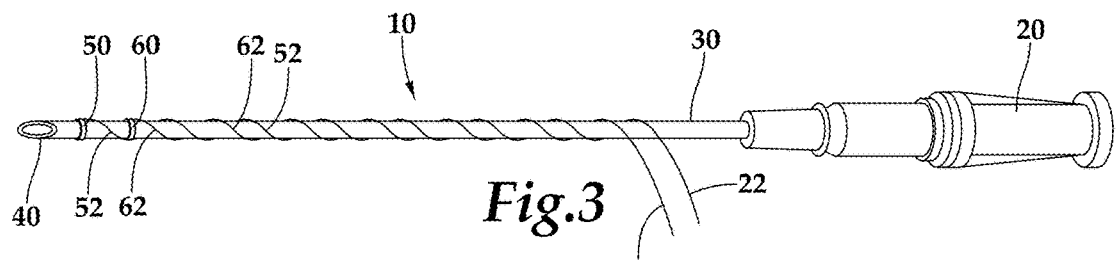
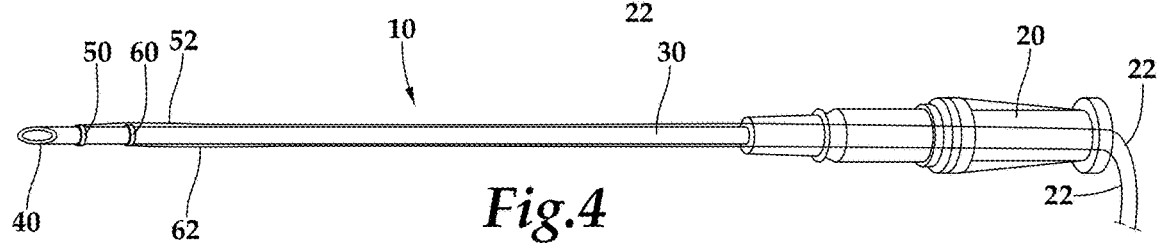
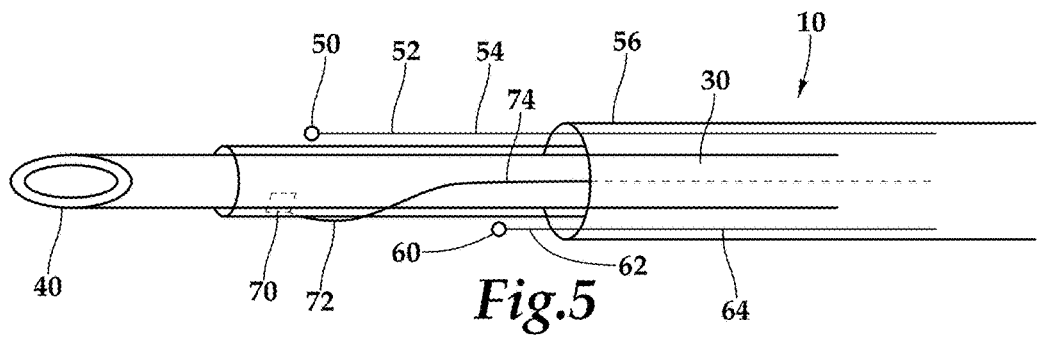
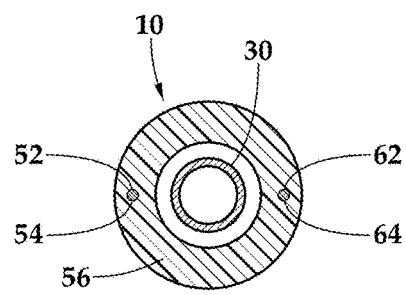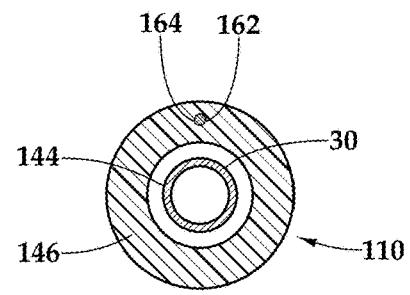
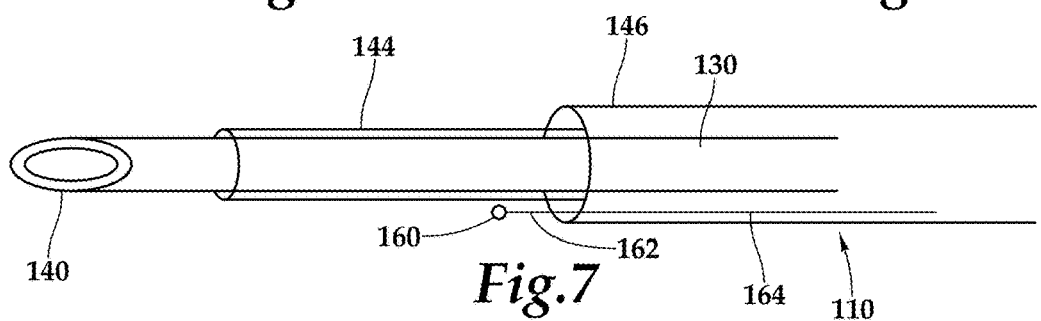
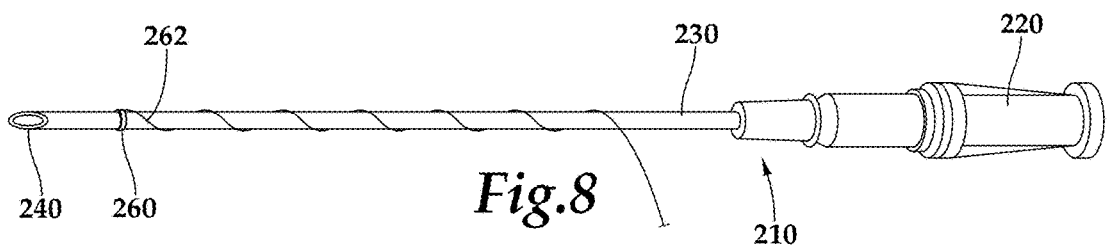

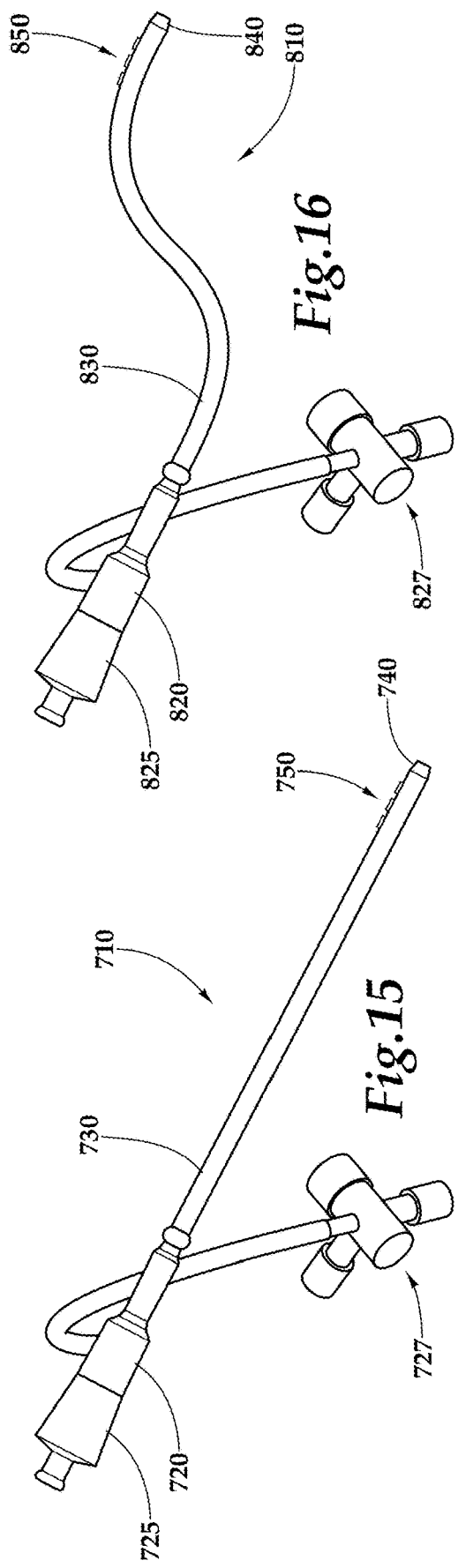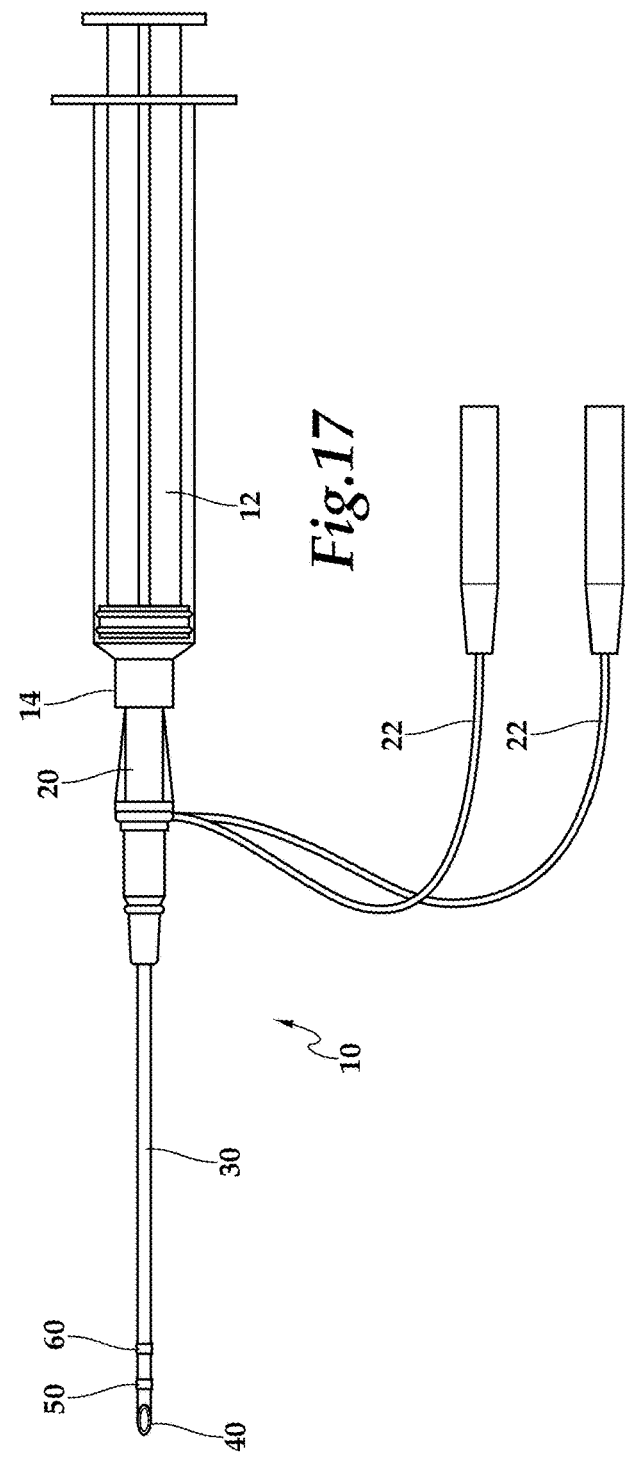

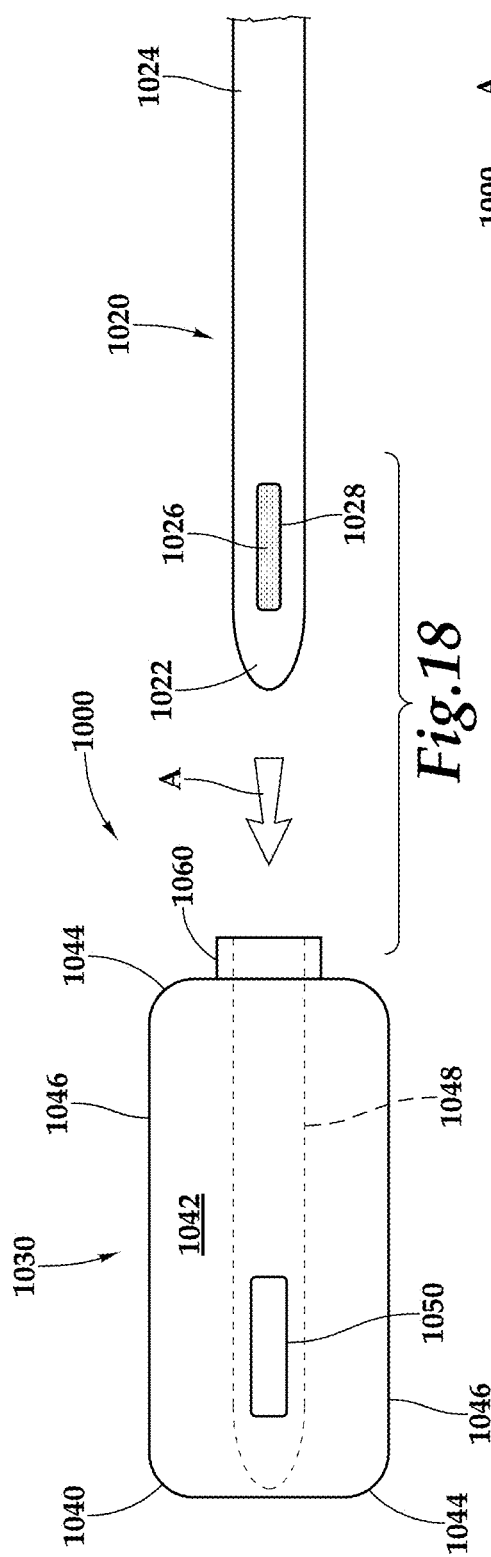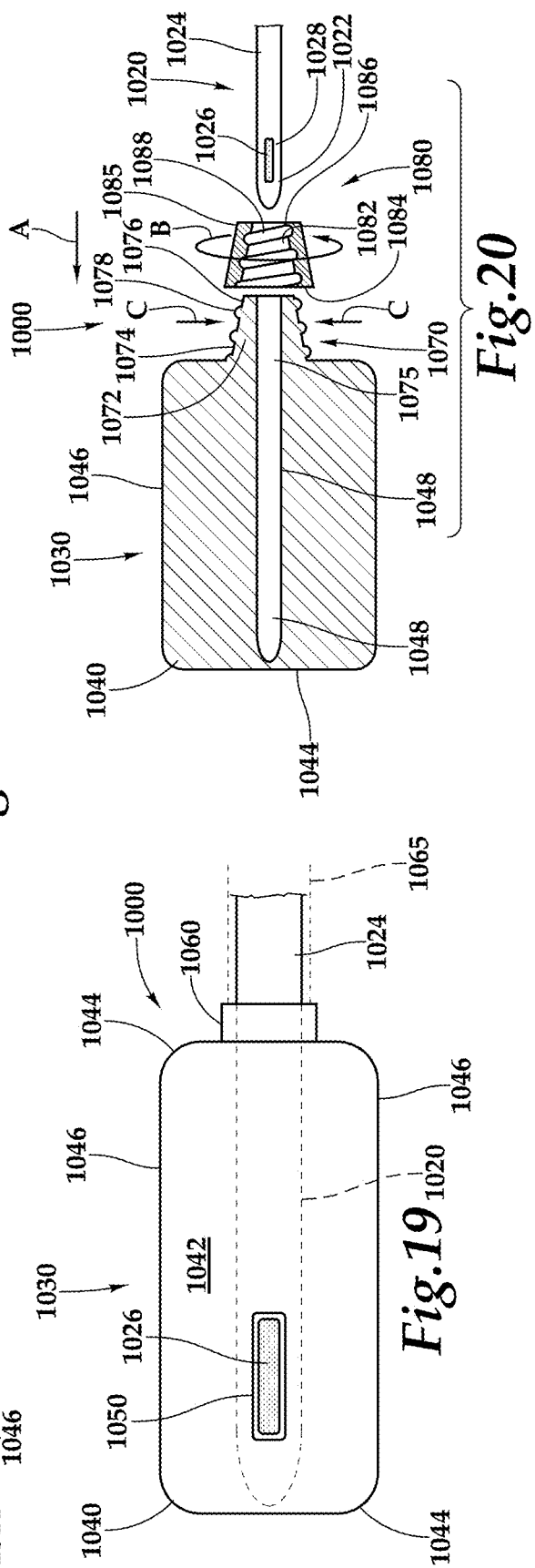

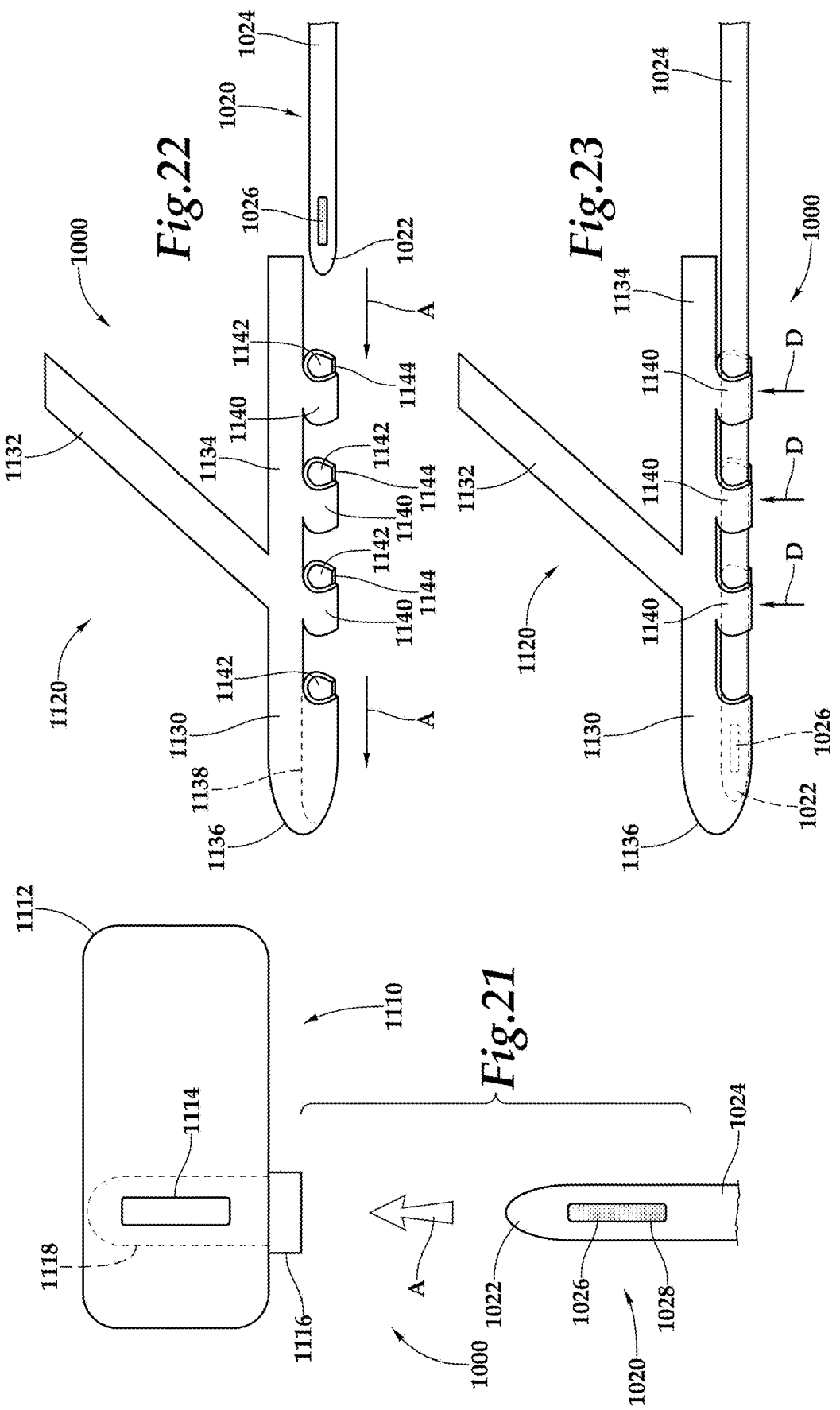

INTRACARDIAC ULTRASOUND CATHETER
HANDHELD ADAPTER

CROSS-REFERENCE TO RELATED APPLICATIONS

This application claims benefit under Title 35, United States Code § 119(e) of U.S. Provisional Application No. 62/633,793 filed on Feb. 22, 2018 and is a continuation-in-part of U.S. patent application Ser. No. 15/713,307 filed on Sep. 22, 2017, which claims benefit under Title 35, United States Code § 119(e) of U.S. Provisional Application No. 62/398,394 filed on Sep. 22, 2016 and U.S. Provisional Application No. 62/516,556 filed on Jun. 7, 2017.

FIELD OF THE INVENTION

This invention relates to use of subcutaneous space visualization tools both for intravascular access, such as with needles, and especially needles fitted with sensors thereon and coupled to electrophysiology mapping systems to identify their position, and imaging tools for intravascular space imaging, and especially intracardiac ultrasonic imaging.

BACKGROUND OF THE INVENTION

Cardiac electrophysiology ablation for the treatment of atrial fibrillation has become mainstream. However, complications from intravascular access and esophageal ulcers are relatively common and can be life threatening. Catheter access to the heart traditionally involve venous and on occasion, arterial access. However, intravascular access can have complications. Groin access is associated with a 4.8% complication rate. These complications can include hematomas, arterial-venous fistulas, pseudoaneurysms, and retroperitoneal bleeding. Internal jugular and subclavian access are also on occasion used during cardiac electrophysiology mapping procedures and can be associated with a 4-20% complication rate. Complications include pneumothorax, hemothorax, carotid and subclavian artery puncture, and hematomas. Additionally, esophageal ulceration following AF ablation is a relatively common occurrence (50%), and atrial esophageal fistula following AF ablation can be fatal. These iatrogenic complications cause significant morbidity and mortality within the hospital. Fluoroscopy is sometimes utilized, but exposes both patient and operator to radiation. CT and MRI guidance have been reported, however would require access to CT/MRI which may not be readily available in the cardiac catheterization lab.

Frequently the cardiac electrophysiology ablation procedure involves using a cardiac electrophysiology mapping system. Cardiac electrophysiology mapping systems use magnetic sensors and/or electrical data (impedence and/or current) for positional data for intracardiac catheters. Commercially available systems include the Carto Biosense Webster System, St Jude Velocity system, and Rhythmia Boston Scientific System. Esophageal catheters can delineate the esophageal lumen but not the outer circumference of the esophagus. Various esophageal protective strategies including esophageal temperature monitoring and physical manipulation of the esophagus have not shown to be conclusively protective of the esophagus.

The Carto Biosense Webster System has a commercially available intracardiac ultrasound catheter which allows for the incorporation of positional information derived from intravascular ultrasound images to be included within the mapping system. Carto Sound can create contours of intracardiac chambers from the intravascular ultrasound with a 16 cm range.

The common femoral vein is a frequent access point for cardiac electrophysiology mapping systems. The common femoral vein ranges in 1.5 cm to 2.5 cm in depth and is associated with body mass index. Commonly, percutaneous needles are 7 cm in length, and sometimes 9 cm length. These are well within the ranges of intravascular ultrasound imaging.

Direct visualization of intravascular access may reduce these complication rates. Current technology uses ultrasound in conjunction with a percutaneous needle to obtain vascular access. However, this technique requires the operator to simultaneously hold the echo probe and percutaneous needle and the echo probe can frequently obstruct the point of access.

The various commercially available cardiac electrophysiology mapping systems use different modalities to identify locality of catheters within the body. The St. Jude ENSITE system, a trademark of St. Jude Medical, Atrial Fibrillation Division, Inc. of St. Paul, Minn., uses impedance to localize various catheters relative to a stable catheter located within the heart. There is a background circuit utilizing a high frequency transthoracic electric field between the catheters and body surface electrodes, which detect impedance changes relative to a stable cardiac catheter (usually located within the coronary sinus) to derive location information within the heart. Consequently, this existing cardiac electrophysiology mapping system can utilize bipolar/unipolar electrode impedance and/or electrical current to determine the location of these electrodes in a three-dimensional space relative to a set of reference electrodes.

Another mapping system produced by Biosense Webster utilizes a magnetic field and a magnetic sensor to localize catheter location. A magnetic field is created around the thorax, and a magnetic sensor equipped catheter within this three-dimensional field is localized to a precision within 1 mm. These mapping systems can combine anatomical information from computer tomographic imaging, fluoroscopy and intravascular echo into the electrical mapping system. These include endocardial, epicardial and importantly pericardial structures, without the need of active fluoroscopy.

Besides vascular injury, esophageal injury from catheter ablation of atrial fibrillation is a feared complication. Direct visualization of the outer circumference of the esophagus, can allow for controlled amounts of energy to be delivered within the posterior wall of the left atria adjacent to the esophagus.

SUMMARY OF THE INVENTION

With this invention, a cardiac electrophysiology mapping system is utilized to visualize blood vessels for percutaneous access. Visualization of the blood vessels can be accomplished by using an intracardiac ultrasound handheld adapter in conjunction with the intracardiac ultrasound catheter (or other intravascular imaging device). This allows for visualization of the blood vessel contours through the cardiac electrophysiology mapping system. A percutaneous needle with mounted magnetic sensors and/or electrodes, as discussed herein, can allow for direct and real time visualization of vessel access on a display of the cardiac electrophysiology mapping system.

The adapter includes a handle preferably with an echogenic window and an at least partially hollow interior to accommodate an intravascular ultrasound catheter. A fastener is preferably provided on the adapter, which can change aperture. The fastener in the open position allows free travel of the intravascular ultrasound catheter. The fastener in the closed position, secures the intravascular ultrasound catheter without damaging the catheter. The adapter body can have different shapes, including but not limited to rectangular, cylindrical, spherical, cube like, grip like, boomerang shaped. The fastener can be a twisting mechanism, cam mechanism, or spring mechanism. The surface with the echogenic window, can be flat or curved. The intracardiac ultrasound adapter can also have a self-sealing feature to not allow air into the space, which can interfere with ultrasound energy. For example, the self-sealing adapter could be a perforated diaphragm. There could also be a tail/sleeve, which can extend further along the length of the intracardiac echo catheter.

In another embodiment, the adapter has an echogenic window and a hollow tube to accommodate an intravascular ultrasound catheter. There is a fastener on the side of the handle, which can change aperture. The fastener in the open position allows free travel of the intravascular ultrasound catheter. The fastener in the closed position, secures the intravascular ultrasound catheter without damaging the catheter. The handle can have different shapes, including rectangular, cylindrical, spherical, cube like, grip like, boomerang shaped. The fastener can be a twisting mechanism, cam mechanism, or spring mechanism. Note the intravascular catheter can enter in any angle. The surface with the echogenic window, can be flat or curved.

In another embodiment, the intravascular ultrasound catheter fits into clasps on an adapter with a wing acting as a handle. The tip of the intravascular ultrasound catheter can be inserted into a secure area that limits longitudinal movement. There can be one or more clasps/prongs, which can be reversibly attached to the ultrasound catheter. The handle could have multiple shapes and curves. The prongs could be laid linearly, or along a curvature. As in previous designs, a fastener could also be used to secure the catheter within the clasps/prongs. The prongs could be connected longitudinally like a clamp. The prongs and/or clamp could be within a groove on the hand held adapter.

Electrophysiology mapping (hereafter EP mapping) systems are provided from multiple sources, as explained above, and generally allow for an intra-vascular/intra-cardio catheter and/or electrode to have its location visualized within the heart. With this invention, an intracardiac ultrasound probe or other imaging tool is outfitted in one of a variety of different manners, at least some of which are similar to the outfitting of catheters and/or electrodes within an EP mapping system which are placed intravascularly into or proximate to the interior of the heart. Also, a pericardiocentesis needle is modified to include at least one electrode thereon or some other sensor, such as a magnetic field sensor. The percutaneous needle can thus also be visualized within the EP mapping system, in one embodiment. Sensors, such as an electrode, which are mounted to then needle, are routed into the EP mapping system, such as in the same way that other electrodes or other sensors within an EP mapping system are integrated into the EP mapping system, such as the way that catheters and intravenous electrodes of EP mapping systems are connected into such EP mapping systems for visualization thereof on a display of the EP mapping system. One such EP mapping system is disclosed in U.S. Pat. No. 8,825,144, incorporated herein by reference in its entirety.

The methodology implemented by this mapping system is based on the principle that when electrical current is applied across two surface electrodes, a voltage gradient is created along the axis between the electrodes. Although any suitable number of electrodes may be utilized, typically six surface electrodes are placed on the body of the patient and in three pairs: anterior to posterior, left to right lateral, and superior (neck) to inferior (left leg). The three electrode pairs form three orthogonal axes (X-Y-Z), with the patient's heart being at least generally at the center.

These six surface electrodes are connected to the EP mapping system. In embodiments, such as those working with the St. Jude ENSITE EP mapping system, the various electrodes alternately send an electrical signal through each pair of surface electrodes to create a voltage gradient along each of the three axes, forming a transthoracic electrical field. Conventional electrophysiology catheters may be connected to the system and advanced to the patient's heart. As a catheter enters the transthoracic field, each catheter electrode senses voltage, timed to the creation of the gradient along each axis. Using the sensed voltages compared to the voltage gradient on all three axes, the three-dimensional position of each catheter electrode is calculated. The calculated position for the various electrodes can occur simultaneously and be repeated many times per second.

The EP mapping system can display the located electrodes as catheter bodies with real-time navigation. By tracking the position of the various catheters, the system provides non-fluoroscopic navigation, mapping, and creation of chamber models that are highly detailed and that have very accurate geometries. In the latter regard, the physician sweeps an appropriate catheter electrode across the heart chamber to outline the structures by relaying the signals to the computer system that then generates the 3-D model. This 3-D model may be utilized for any appropriate purpose, for instance to help the physician guide an ablation catheter to a heart location where treatment is desired.

In order to generate an accurate and highly detailed map of a patient's heart, a large amount of data is required. Accordingly, an electrode catheter may be swept across various surfaces of the heart while obtaining data as described above. In order to accelerate this mapping data acquisition and/or increase the volume of data available for mapping, a number of high-density electrode catheters have been developed or proposed. Generally, these include a number of electrodes in an array in relation to a catheter body so as to substantially simultaneously obtain many mapping data points for a corresponding surface of cardiac tissue proximate to the catheter body. For example, these electrodes may be deployed along the length of a section of the catheter body that has a coil or other three-dimensional configuration so as to provide the desired spatial distribution of the electrodes. Alternatively, the electrodes may be disposed on a number of structural elements extending from a catheter body, e.g., in the form of a basket or a number of fingers.

Once the mapping data has been acquired, software may be implemented to generate multiple surface images, which when combined, comprise a three-dimensional image of the patient's heart. This image can be displayed on a suitable output device in real-time so that the physician can "see" the patient's heart and the catheter for properly positioning the catheter at an intravascular procedure location, such as within the patient's heart for a medical procedure (e.g., an ablation procedure).

The electrode or other sensor on the needle (and/or the intracardiac ultrasound probe or other intravascular imaging tool) causes the location of the electrode relative to adjacent cardiac structures to be visualized on the display of the EP mapping system. By placing the electrode on the percutaneous needle, such as at a known distance from a tip of the needle, and by knowing the orientation of the needle, the precise location of the tip of the needle can be known and visualized on the EP mapping system display. Knowing orientation of the needle can occur by having multiple electrodes on the needle, one distal and one proximal, so that the orientation of the needle is merely a line segment between the position of the two electrodes, or can be ascertained in some other fashion, such as by having a needle orientation sensor placed on the needle itself or other sensor physically attached to the needle. In one embodiment one of the electrodes can be the tip of the needle itself. By visualizing on the display the location of the tip of the percutaneous needle in real time, a surgeon or other medical professional can precisely place the tip of the needle where desired relative to safely gain vascular access, such as at the femoral vein or femoral artery or at other locations.

In certain environments, other imaging systems can be incorporated along with the EP mapping system, such as CT scans, MRI scans, ultrasound, fluoroscopy, etc. While the invention is described above in particular with regard to intracardiac ultrasound probes and percutaneous needles, other interventional devices have a transcutaneous or intravascular nature can similarly be outfitted with electrodes or other sensors and integrated into the EP mapping system for visualization of location (and preferably also orientation) of such other devices. Such other devices include dilators, sheaths, catheters, stylets associated with needles and dilators, imaging devices and other transcutaneous interventional devices. When EP mapping systems are referenced, these can be electric field based or magnetic field based, as described above (or some combination thereof).

According to one method of use of this invention, a further description of this invention is provided.

Patient Population

Any patient requiring intravascular access:

1. Patients undergoing electrophysiology studies and ablations.
2. Patients who are need of accurate vascular access
3. Patients undergoing AF ablation Protocol 1. The described protocol will use the Biosense Webster Carto System.
2. Magnet for cardiac electrophysiology system is placed under the pelvis.
3. Posterior magnetic patches are placed on the buttocks/back of leg and sacrum.
4. If needed, anterior patches can be placed on the legs and suprapubic areas.
5. EP mapping system and echo machine is initialized, using standard protocol.
6. Standard prep for intravascular access in cardiac catheterization lab.
7. Intracardiac ultrasound catheter such as Carto Sound Star is inserted into the intracardiac ultrasound catheter adapter and secured.
8. Images of blood vessels are obtained using the combined intracardiac ultrasound catheter and adapter.
9. Vessel circumference is obtained in the cardiac electrophysiology mapping system.
10. The intracardiac ultrasound and adapter is removed from the site.
11. The intracardiac ultrasound is disconnected from the adapter, and set aside to be used for intravascular purposes later.
12. Percutaneous needle with mounted magnetic sensors and/or electrodes is connected to the cardiac electrophysiology mapping system.
13. The operator directly and in real time visualizes percutaneous needle with mounted magnetic sensor and/or electrodes on the cardiac electrophysiology mapping system as access is obtained of the vessel of interest.
14. Standard J wires, dilators and sheaths can be used to complete vascular access to accommodate catheters.
15. This can be repeated until all sheaths are in place.
16. Cardiac procedure is performed at discretion of the operator, and the intra-vascular catheter can be reused during the same procedure.
17. If atrial fibrillation ablation is performed, intraesophageal ultrasound examination can be performed, with contours of the esophagus and left atria placed into the cardiac electrophysiology mapping system.

In one embodiment, a switch between two or more magnets for the cardiac electrophysiology mapping system can occur. During vessel access, the first magnet can be used. Once vessel access is achieved, the switch can change to the second magnet, which would allow for electrical anatomical mapping of cardiac structures. Optionally, a rail system for the cardiac electrophysiology mapping system can be placed under the procedure table. The cardiac electrophysiology mapping system magnet could be moved along the rail which could travel the length of the patient, for example, between the femoral veins and the heart, to focus the EP mapping system at a location of interest for imaging and support of procedures being performed.

Also with this invention, a magnetic sensor with or without electrodes is mounted on a transesophageal echo probe or intraesophageal ultrasound probe to delineate the various layers including the outer circumference of the esophagus, and possibly the pericardium, epicardium, and endocardium to guide the intensity of ablative energy and force applied to the posterior wall of the left atria. The goal being to decrease the probability of esophageal injury during ablation for atrial fibrillation.

A magnetic sensor can be attached to a transesophageal echo or intraesophageal ultrasound probe. Circumferential contours of the esophagus can be obtained, both luminal and outer circumference. If available, pericardial, epicardial and endocardial contours can also be obtained. These contours could be displayed in a cardiac electrophysiology mapping system. The intraesophageal ultrasound transducer can be rotational either manually or spun on a rotary motor to obtain up to a 360 degree view of the esophagus or a phased array to produce 2 dimensional views of the esophagus and surrounding structures.

The intraesophageal ultrasound can produce images similar to radial endoscopic images which can visualize the contours of the esophagus and possibly the left atria. There can be a reference point for orientation with the magnetic sensors within the cardiac electrophysiology mapping system, so that anatomical structures such as the left atria can be readily identified. The transesophageal ultrasound can be equipped with a phased array which can be oriented parallel (as shown above) or perpendicular to the catheter long axis, or both orientations to give a 2-dimensional or 3-dimensional view of the esophagus/pericardial/left atria interface. The phased array could also be adjustable, similar to standard transesophageal echo probes.

The transesophageal echo mounted magnetic sensors deliver images similar to currently available transesophageal echo probes. The ultrasound transducer could be located on the tip, or anywhere along the body of the esophageal catheter. The probe can be maneuvered along the length of the esophagus to obtain the esophageal lumen, outer circumference of the esophagus, and the layers of the left atria myocardium. In addition, circumferential measurements of the esophagus can be made during contraction and dilation phases of the esophagus. The intraesophageal ultrasound probe can have one or more electrodes and magnetic sensors that are similar to commercial esophageal mapping catheters, which will allow for visualization of the echo/ultrasound images on a cardiac electrophysiology mapping system. The catheter can be configured to be deflectable to allow steerability in one or more planes. The electrodes and magnetic sensors could be located anywhere along the tip or body of the catheter.

The esophageal catheter can have a combination of ultrasound transducers arranged in a radial orientation, rotational on a spinning tip, and/or linear in orientation. For example, a rotational transducer can produce an image of the esophagus relative to the left atria, while linear transducers with an ice pick view, can potentially take advantage of ultrasound thermometry in the outer circumference of the esophagus.

The catheter could also have a port to allow for suction, so that the esophagus can collapse around the catheter for better contact and imaging. This may also have the action of drawing the esophagus away from the posterior aspect of the left atria. The catheter can have mounted balloons proximally and or distally, to allow for a pressure seal within the esophagus lumen. The mounted balloon could also be placed at the transducer location to allow for good tissue contact and stable placement.

Intravascular access is a compulsory component to electrophysiology studies and ablation. Significant morbidity and mortality can arise from intravascular access. Using a cardiac electrophysiology mapping system to visualize relevant blood vessels will likely reduce these complications. Visualization of the blood vessels in multiple locations from the surface can be accomplished with commercially available intracardiac echo catheters in combination with the proposed intracardiac ultrasound handheld adapter. The images of the blood vessels can be obtained, and their contours recorded into the cardiac electrophysiology mapping system. A percutaneous needle with mounted magnetic sensor and/or electrodes allows for real-time visualization of intravascular access.

According to the prior art, intravascular access is obtained by an anatomical approach, ultrasound guidance, or a combination of both. The anatomical approach allows for freedom of both operator hands, and an obstruction free access site, however without direct visualization of the tip. The ultrasound guidance approach potentially allows for direct visualization of the needle. However visualization of the tip is inconsistent, the surface ultrasound probe blocks part of the access site, and one of the operator's hands needs to be used to operate the probe.

The intracardiac ultrasound catheter handheld adapter allows for obtaining anatomical information of the vessels for intravascular access into a cardiac electrophysiology mapping system. In combination with the magnetic sensor and/or electrode mounted percutaneous need, real time visualization of vessel access can be obtained, without obstruction of the access site and allows both hands to be used for the operator. This allows for the advantages of the anatomical and ultrasound approach, without the disadvantages of both approaches.

The magnetic sensor and/or electrode mounted percutaneous needle can be reused for multiple access sites. Once intravascular access is obtained, the same intracardiac ultrasound catheter can be reused in the same patient for intravascular imaging.

The intracardiac ultrasound catheter handheld adapter in combination with the previously proposed magnetic sensor and/or electrode mounted percutaneous needle leverages the cardiac electrophysiology mapping system to allow for increased precision of intravascular access which would likely reduce complications related to intravascular access, and have broad applicability in the cardiac electrophysiology lab.

The magnetic sensor mounted transesophageal echo or intraesophageal ultrasound can accurately image the outer circumference relative to the left atria. Current esophageal protection strategies using temperature probes and maneuvering the esophagus has not been conclusively shown to protect the esophagus. This could be because these protective mechanisms are luminal in nature, however the outer esophagus is not visualized during ablative procedures. Accurate imaging of the outer circumference of the esophagus will allow for increased guidance in ablative energy application when applied in the left atria and in proximity to the esophagus.

The magnetic sensor mounted transesophageal echo or intraesophageal ultrasound allows for accurate imaging of the outer diameter of the esophagus, and with previously proposed left atria thickness maps, can allow for full thickness ablation of the left atria myocardium, while protecting the esophagus.

OBJECTS OF THE INVENTION

Accordingly, a primary object of the present invention is to provide an adapter which allows an intracardiac ultrasound probe to be used supracutaneously before using a percutaneous access needle to gain vascular access.

Another object of the present invention is to provide an adapter which can both allow visualization of a vascular access site in a first step, and then have the adapter removed and the intracardiac (or other intravascular) ultrasound (or other imaging tool) be routed intravascularly for further use in intravascular imaging.

Another object of the present invention is to provide a single imaging tool which can be used both to assist in vascular access imaging and then later in a related procedure provide intravascular imaging.

Another object of the present invention is to provide an imaging tool which can be coupled to an EP mapping system to allow the EP mapping system to provide imaging in support of effective vascular access establishment.

Another object of the present invention is to provide an imaging tool coupled to an EP mapping system which can remain coupled to the EP mapping system during a first phase when the imaging tool is used to image a vascular access location and also in a second phase when the imaging tool is used intravascularly.

Another object of the present invention is to provide an adapter covering an intercardiac ultrasound probe or other imaging tool which allows the imaging tool to be used supracutaneously, and then have the adapter removed and the intravascular imaging tool be sanitary and otherwise ready for use intravascularly.

Another object of the present invention is to improve outcomes in intracardiac procedures by utilizing an intracardiac imaging tool, such as an inter-cardiac ultrasound probe before the intracardiac procedure is performed to image a luminal access site and/or guide a luminal access tool (such as a percutaneous needle) when gaining luminal access for performance of the cardiac procedure.

Another object of the present invention is to provide a vascular access needle with electrodes and/or magnetic field sensors included thereon, so that the vascular access needle can be visualized on an EP mapping system during its use, to gain vascular access at a luminal access site, including a luminal access site which has been previously visualized by an imaging tool, such as an intracardiac ultrasound probe used supracutaneously.

Another object of the present invention is to provide a percutaneous needle or other transcutaneous interventional device which is fitted with electrodes are other sensors so that it can be visualized through an EP mapping system display for most accurate, reliable and safe placement of the tip of the needle or other device.

Another object of the present invention is to provide a percutaneous needle with at least one electrode thereon coupled to an EP mapping system with location of the needle presented within a display of the system.

Another object of the present invention is to provide a needle equipped with bipolar/unipolar electrodes which can monitor impedance and/or electrical current for positioning the needle in an EP mapping system display.

Another object of the present invention is to provide a system where the impedance and/or electrical current data from sensors on the needle or other device can be utilized by existing cardiac electrophysiology mapping technologies to visualize the needle tip entry into vascular or other lumen space.

Another object of the present invention is to provide a needle equipped with at least one magnetic sensor to convey locational information in a magnetic field.

Another object of the present invention is to provide magnetic data that can be utilized by existing cardiac electrophysiology mapping technologies to visualize the needle tip entry into a subcutaneous luminal space.

Another object of the present invention is to provide magnetic data that can be utilized by existing cardiac EP mapping technologies to visualize dilator entry into an intravascular space.

Another object of the present invention is to provide a sheath equipped with at least one magnetic sensor to convey locational information in a magnetic field.

Another object of the present invention is to provide magnetic data that can be utilized by existing cardiac EP mapping technologies to visualize sheath entry into an intravascular space.

Another object of the present invention is to provide an esophageal ultrasound probe fitted with electrodes and/or magnetic sensors coupled to an EP mapping system to locate ultrasound data to assist in protection of the esophagus during atrial ablation procedures and other procedures where esophageal imaging is beneficial.

Other further objects of the present invention will become apparent from a careful reading of the included drawing figures, the claims and detailed description of the invention.

BRIEF DESCRIPTION OF THE DRAWINGS

FIG. 3 is a perspective view of a pericardiocentesis needle according to a first embodiment of this invention, the pericardiocentesis needle modifiable in form and size to be a percutaneous luminal access needle.

FIG. 4 is a perspective view of a modified version of that which is shown in FIG. 3, the pericardiocentesis needle modifiable in form and size to be a percutaneous luminal access needle.

FIG. 5 is a detail of a portion of that which is shown in FIG. 3, and with electrodes shown schematically, the pericardiocentesis needle modifiable in form and size to be a percutaneous luminal access needle.

FIG. 6 is an end full sectional view of an embodiment of that which is shown in FIG. 3, which has both a proximal electrode and a distal electrode, the pericardiocentesis needle modifiable in form and size to be a percutaneous luminal access needle.

FIG. 7 is a perspective view of an embodiment of that which is shown in FIG. 3 which has a single electrode depicted schematically thereon, and where a tip of the needle can be an electrode, the pericardiocentesis needle modifiable in form and size to be a percutaneous luminal access needle.

FIG. 8 is a perspective view of a modified version of that which is shown in FIG. 7.

FIG. 9 is an end full sectional view of that which is shown in FIG. 7.

FIG. 15 is a perspective view of a sheath assembly with magnetic field sensors shown thereon as one form of sensors for visualizing a location of a tip of the sheath assembly according to one embodiment of this invention.

FIG. 16 is a perspective view of that which is shown in FIG. 15, but for a sheath having a curving contour.

FIG. 17 is a front elevation view of a variation of the needle of FIG. 3 with a syringe attached to a hub of the needle and with leads extending from the hub for interfacing into an EP mapping system, the pericardiocentesis needle modifiable in form and size to be a percutaneous luminal access needle.

FIG. 18 is it an exploded parts view of an intracardiac ultrasound probe and adapter according to this invention and before placement of the intracardiac ultrasound probe tip into the adapter.

FIG. 19 is a plan view of an intracardiac ultrasound probe which has been inserted into a handheld adapter according to one embodiment of this invention.

FIG. 20 is a full sectional plan view of an alternative embodiment of that which is shown in FIG. 2, and with an intracardiac ultrasound probe exploded away from the adapter.

FIG. 21 is an exploded parts view of an intracardiac ultrasound probe and adapter exploded apart, and with the adapter configured according to an alternative embodiment of that which is disclosed in FIG. 1.

FIG. 22 is an exploded parts view of an intracardiac ultrasound probe and a further alternative embodiment adapter for use with the ultrasound probe.

FIG. 23 is a plan view of that which is shown in FIG. 22, but with the intracardiac ultrasound probe fully inserted into the adapter of FIG. 22.

DESCRIPTION OF THE PREFERRED EMBODIMENT

Figure 1:
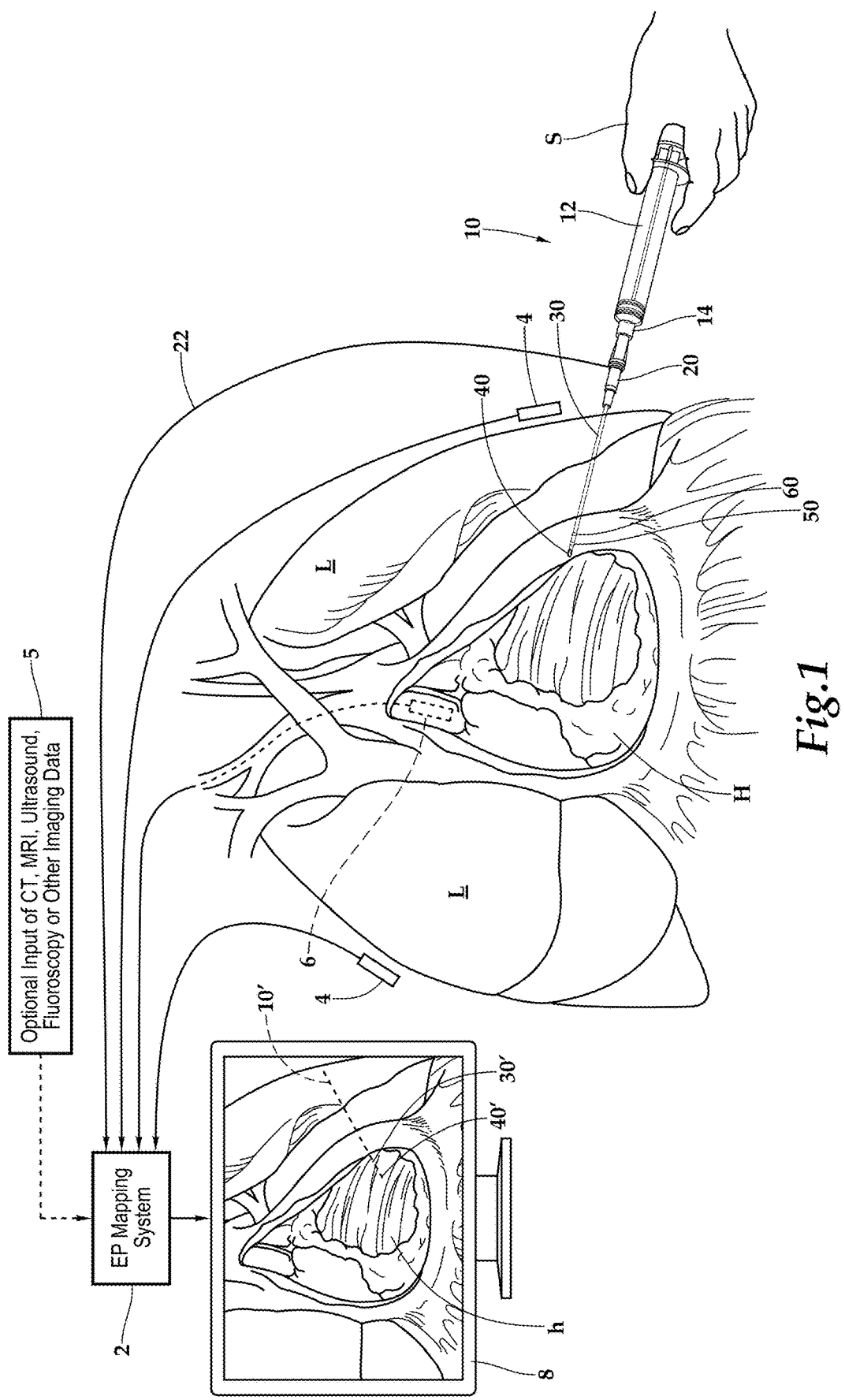
FIG. 1 is a schematic depiction of the system of this invention including a portion of a torso of a patient with a pericardiocentesis needle fitted with sensors in the form of electrodes shown engaging bodily structures proximate to the heart of a patient, and while the needle is visualized on a display of an EP mapping system, the EP mapping system relying primarily upon electrodes for generating the image displayed on the EP mapping system display, the pericardiocentesis needle modifiable in form and size to be a percutaneous luminal access needle.

Referring to the drawings, wherein like reference numerals represent like parts throughout the various drawing figures, reference numeral 1000 is directed to a visualization system for visualization of various subcutaneous spaces (FIGS. 18-20 and 24). The system 1000 utilizes an imaging tool such as an intracardiac ultrasound probe 1020 twice during an intravascular procedure. The probe 1020 or other imaging tool is first used during gaining of vascular access, such as with a percutaneous vascular access needle 10 (FIG. 24), and with the probe 1020 or other imaging tool first covered by an adapter 1030. The probe 1020 or other imaging tool is second used with the adapter 1030 removed by insertion intravascularly and routed to an intra-vascular procedure visualization location. The intracardiac ultrasound probe 1020 is preferably coupled to an EP mapping system 1320 (FIG. 24) both during supra-cutaneous use at the access site and during intravascular use, such as within or adjacent to an intracardiac space.

In essence, and with particular reference to FIGS. 18-20 and 24, basic details of the system 1000 of this invention are described, according to a first embodiment. The system 1000 generally includes two main parts including an intracardiac ultrasound probe 1020 and an adapter 1030. The intracardiac ultrasound probe 1020 provides one form of imaging tool which can be integrated into an EP mapping system 1320, or can be used independently. The adapter 1030 is removable from the probe 1020 or other imaging tool. The adapter 1030 includes a body 1040 providing a suitable handheld housing for use of the probe 1020 supracutaneously, such as for imaging a luminal access site, such as adjacent to the femoral artery and femoral vein. The body 1040 includes a window 1050 therein which is echogenic to facilitate ultrasound imaging therethrough.

An interface 1060 on the body 1040 allows for removable attachment of the adapter 1030 securely to the probe 1020. An alternate interface 1070 (FIG. 3) features a tight enable nut 1080 to allow for the alternate interface 1070 to clamp down onto the probe 1020 when the nut 1080 is tightened, for removable connection of the adapter 1030 to the probe 1020. Other forms of alternate adapters are also disclosed herein.

The system 1000 is preferably configured for use within an EP mapping procedure suite 1300 (FIG. 24) which typically includes a surgical table 1310 and an EP mapping system 1320 with included monitor 1330. A primary magnet 1340 associated with the table 1310 can, in one form of this invention be movable for proper placement of the primary magnet 1340 both at a luminal access site, such as the femoral vein or artery, and at a location closer to a procedure site, such as adjacent to the thoracic cavity of the patient.

More specifically, and with particular reference to FIGS. 1-17, details of a pericardiocentesis needle are disclosed, which needle can be appropriately modified to be a percutaneous vascular access needle 10 (FIG. 24) which can be imaged, such as with an EP mapping system 1320, for use at a luminal access site after appropriate imaging with the system 1000 (FIGS. 18-27) including the intracardiac ultrasound probe 1020 and associated adapter 1030.

In essence, and with particular reference to FIG. 1, basic details of the needle 10 and associated EP mapping system 2 as modified by one embodiment of this invention, is described. The EP mapping system 2 includes multiple surface electrodes 4, as well as intracardiac electrodes 6 (and optionally also auxiliary input 5 of imaging data) to gather data for presentation on a display 8. The needle 10 is modified according to this invention so that it can be visualized on the display 8 of the EP mapping system 2. The needle 10 includes a hub 20 with a shaft 30 extending from the hub 20 to a tip 40. In this embodiment, at least one electrode, and preferably both a distal electrode 50 and proximal electrode 60, are placed along the shaft 30. These two electrodes 50, 60 measure electric field intensity (or current or other electrical properties) and supply this information to the EP mapping system 2 so that a position, and also preferably orientation, of the needle 10 can be determined and be displayed on the display 8, and especially a location of the tip 40 of the needle 10 relative to other cardiac structures included on the display 8.

Figure 2:
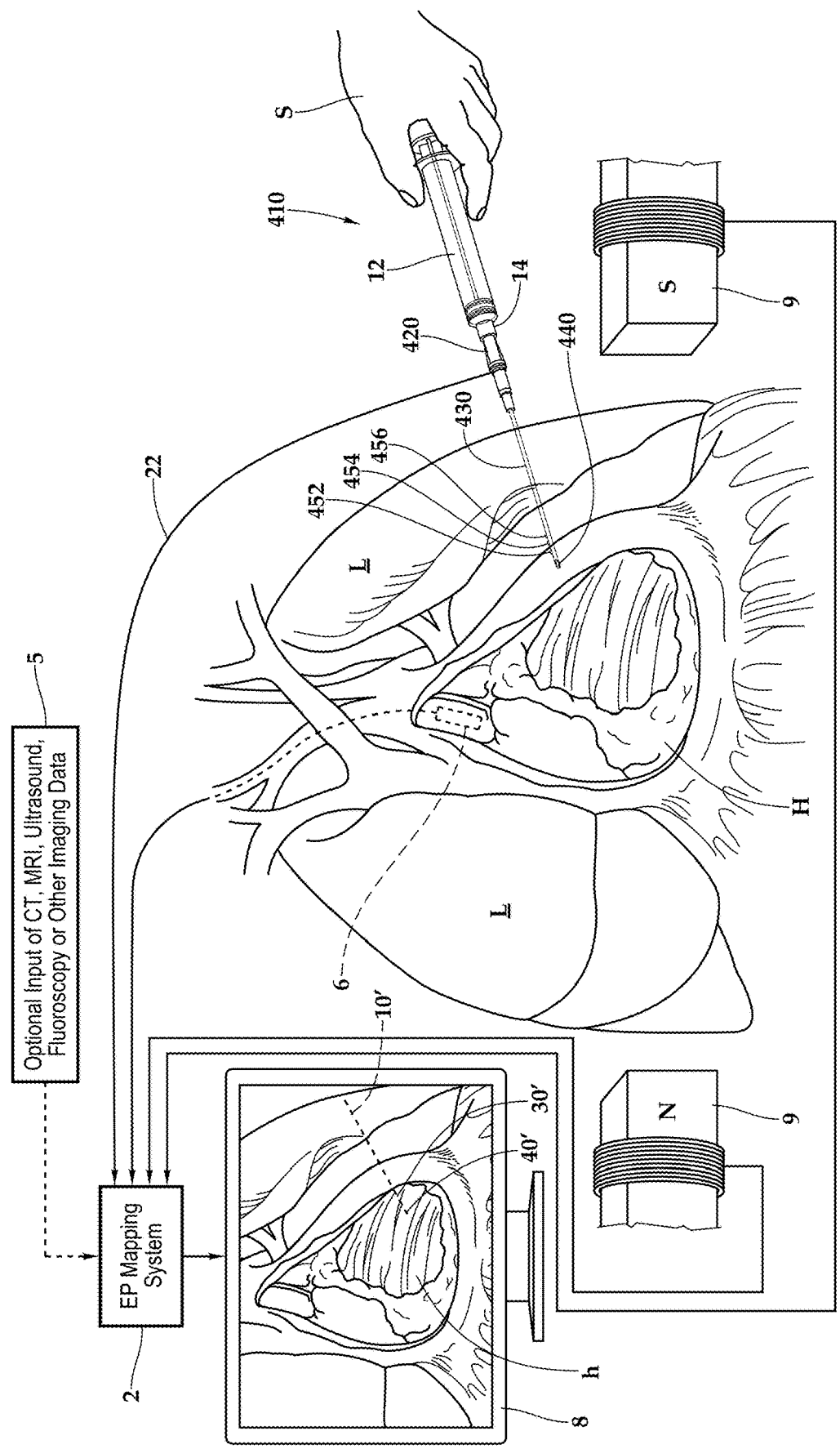
FIG. 2 is a schematic similar to that depicted in FIG. 1, but for an EP mapping system which primarily generates an image of cardiac structures based on placement of a magnetic field proximate to the patient and utilizing magnetic field sensors to localize the pericardiocentesis needle within the image displayed by the EP mapping system, the pericardiocentesis needle modifiable in form and size to be a percutaneous luminal access needle.

More specifically, and with particular reference to FIGS. 1 and 2, basic details of various EP mapping systems 2 are described, with which the needle 10 or other medical device of this invention is configured to interoperably perform. The EP mapping system 2 can be any of a variety of different medical visualization systems, but most preferably those which utilize electric and or magnetic fields to determine the location of bodily structures, and in this case, particularly cardiac structures of a patient.

As a general outline, the EP mapping system 2 can include a plurality of electrodes 4 in the form of surface electrodes on a surface of the patient. FIG. 1 depicts two such surface electrodes 4, but typically more than two such surface electrodes 4 would be utilized. Also, an intracardiac electrode 6 is typically also passed intravenously to a position within or adjacent to the heart H of the patient.

As explained in detail hereinabove, in one embodiment certain pairs of electrodes, such as the surface electrodes 4, switch between providing an excitation voltage resulting in the production of an electric field, and operating in a sensing mode wherever the electrodes sense voltage and/or current or other electrical properties at the locations of various electrodes. Together these electrodes, when switching between an excitation function and a sensing function, gather data about cardiac structures and other subcutaneous structures having different electrical properties, which data is converted into imagery suitable for presentation on the display 8 of the EP mapping system 2.

In one embodiment depicted in FIG. 2, the EP mapping system 2 either replaces the electrodes 4, 6 with magnetic field inducing elements such as magnets 9, or such magnetic field sources 9 augment an EP mapping system 2 which also includes electrodes 4, 6. Furthermore, cardiac structural data can be augmented with information from an auxiliary imaging source 5 and put into the EP mapping system 2. Such auxiliary input 5 can be provided from imaging devices such as computer tomography (CT), magnetic resonance imaging (MRI), ultrasound, fluoroscopy, or other imaging data.

Importantly with this invention, and as described below, the needle 10 or other transcutaneous medical device is fitted with electrodes 50, 60 or other sensors so that a position (and also preferably orientation) of the needle 10, and especially a tip 40 of the needle 10 can be visualized on the display 8 at an accurate position adjacent to heart H structures so that a position (and also preferably orientation) of the needle 10, and especially a tip 40 of the needle 10 can be visualized on the display 8 at an accurate position adjacent to the heart H and other bodily structures. On the display 8, the needle 10 appears as the needle 10' with the tip 40 appearing as a tip 40' and the shaft 30 of the needle 10 appearing as shaft 30'. A user, such as a surgeon S, can thus accurately position the needle 10 by viewing the display 8 of the EP mapping system 2 and moving the needle 10 to cause the tip 40 to be positioned where desired, while watching the display 8.

With continuing reference to FIG. 1, as well as FIG. 17, the needle 10 is described according to an initial exemplary embodiment. The needle 10 includes the hub 20 which supports the shaft 30 extending from the hub 20 to a tip 40. The hub 20 is configured to attach to other fluid handling structures, such as a syringe 12, such as through a luer fitting 14. The hub 20 also preferably has leads 22 which can extend to the EP mapping system 2, and which also connect to electrodes (or other sensors) on the needle 10. In this initial exemplary embodiment, the electrodes include a distal electrode 50 and a proximal electrode 60. By providing two electrodes 50, 60, when their position is determined a line segment between these two electrodes 50, 60 defines a central axis of the shaft 30 of the needle 10. Also, by knowing a distance that the tip 40 is spaced away from the distal electrode 50 (or other reference point), a position of the tip 40 can be precisely determined. This information can be superimposed into the imaging data set which is displayed in the display 8 of the EP mapping system 2, so that a needle 10', as well as a tip 40' of the shaft 30' can all be visualized (FIG. 1), even though no electrode is at the tip 40 of the needle 10.

While it is conceivable that the electrodes 50, 60 could have their own power supply and transmit signals associated therewith wirelessly to the EP mapping system 2, typically the electrodes 50, 60 are connected by a conducting wire 52, 62 from the electrodes 50, 60 through the leads 22 to the EP mapping system 2. FIG. 17 shows two such leads 22 which couple to the wires 52, 62 (FIG. 3) and which lead to the EP mapping system 2, such as along lead 22 (shown as a single line for convenience).

With particular reference to FIG. 3, a simplest form of the needle 10 with two electrodes 50, 60 coupleable to the EP mapping system 2 through external wires 52, 62 is disclosed. These wires 52, 62 are just left external to the shaft 30 of the needle 10 in this embodiment. Such an embodiment would typically perhaps only be used for testing, but could conceivably be utilized for therapeutic purposes. The wires 52, 62 might conceivably be left without any insulation jacket 54, 64 around the wires 52, 62, especially if the shaft 30 of the needle 10 is formed of a non-conducting material. However, typically these wires 52, 62 are encased within their own insulation jackets 54, 64 (FIG. 5). Also, these wires 52, 62 are preferably contained within an outer insulation 56 lining which holds the wires 52, 62 directly adjacent to the shaft 30.

Electrodes 50, 60 themselves could have any of a variety of different configurations, including configurations where they are flush with a surface of the shaft 30 of the needle 10, and embodiments where these electrodes 50, 60 extend outwardly, at least somewhat. In FIGS. 1-4, these electrodes 50, 60 are depicted as having a toroidal form and extending only very slightly away from the surface of the shaft 30. Most preferably, these electrodes 50, 60 are isolated from the shaft 30 of the needle 10 itself. For instance, and as depicted in FIG. 5, an inner lining of insulation can be provided directly adjacent to the shaft 30 of the needle 10. The electrodes 50, 60 are outboard of this innermost insulation lining. The wires 52, 62 are preferably provided with insulation jackets 54, 64 so that if these wires 52, 62 come into contact with each other, electric current is prevented from flowing therebetween. Finally, the outer insulation 56 is preferably provided to encase the wires 52, 62 and their associated insulation jackets 54, 64 are isolated from surrounding structures that the needle 10 might come in contact with. If the shaft 30 of the needle 10 is formed of non-conductive material, the innermost layer of insulation (FIG. 5) can be dispensed with.

The two electrodes 50, 60 are preferably provided a known distance apart from each other and with the distal electrode 50 a known distance away from the tip 40. For instance, the distal electrode 50 can be one inch away from the tip 40 and the proximal electrode 60 can be placed one inch away from the distal electrode 50. Such known distances between the electrodes 50, 60 and away from the tip 40 allow for accurate visualization of location and orientation of the tip 40 of the needle 10 on the display 8. As an example, if the shaft 30 of a needle 10 is extending along a central axis, with a proximal electrode 60 at an origin on the central axis, and the distal electrode 50 is at a one inch mark on this axis, it is known that the tip 40 will be at the two inch mark on this central axis. The coordinates of this central axis can be associated with what is fed to the display 8, and not only the positions of the electrodes 50, 60 can be provided, but also a virtual needle 10' can be animated and presented on the display 8, with the needle 10' extending right up to the tip 40'.

Bodily structures on the display 8 might hide the needle 10' at least somewhat. Known techniques with EP mapping systems 2 can be utilized to make sure that important structures can still be visualized. As one option, body structures "in front of" the portions of the needle 10' adjacent to the tip 40' can be cut away so that the tip 40' of the needle 10' can be seen. As another alternative, at least portions of the needle 10' can be shown in a phantom or broken line manner which perhaps becomes more pronounced or less pronounced based on a depth of the needle away from a view and perspective point, to represent depth. As another option, video editing tools can be utilized by a user to selectively remove bodily structures presented on the display 8 in a customizable fashion to display what the surgeon S or other medical practitioner wants to see, but remove enough detail so that important portions of the needle 10' can be clearly seen.

In FIG. 4 a variation of the needle 10 is displayed where the wires 52, 62 are held adjacent to the shaft 30, such as by placement inboard of outer insulation 56 (FIG. 5). The wires 52, 62 coupled to the electrodes 50, 60 are routed through the hub 20 in this embodiment, where they transition into the leads 22 extending to the EP mapping system. FIG. 5 further depicts, somewhat schematically, how different layers of insulation including innermost insulation and outer insulation 56 are located inboard and outboard of the electrodes 50, 60 and with the outer insulation 56 stopping short of positions for the electrodes 50, 60 so that the electrodes 50, 60 are not blocked from sensing electrical characteristics of bodily structures adjacent to the needle 10 and sensing the electric field sufficiently precisely to allow the electrodes 50, 60 to be located within a three-dimensional space adjacent to the heart H of a patient, without disruption by the electrically insulative character of the other insulation 56. Electrodes in FIG. 5 are seen schematically, rather than with any particular geometric configuration. FIG. 6 depicts how the wires 52, 62 and associated insulation jackets 54, 64 are located outboard of the shaft 30 but inboard of outer insulation 56 which is wrapped around an outer side of the wires 52, 62, or has the wires 52, 62 embedded within the outer insulation 56.

FIG. 5 also shows an optional additional sensor in the form of a force sensor 70. This force sensor 70 can be a strain gauge mounted to the shaft 30 of the needle 10, or some other force sensor 70. The force sensor 70 detects compression forces between the tip 40 and the hub 20. For instance, and especially when the tip 40 is large or less sharp, the tip 40 does not penetrate bodily tissues unless sufficient force is applied. In some instances, it is desirable to penetrate some tissues, but not others. For instance, when performing pericardiocentesis, the skin and surface anatomy, and the pericardium are penetrated, but one does not want to penetrate the myocardium. The force sensor transmits a signal, typically along a wire 72 inside of an insulation jacket 74 to the EP mapping system 2 or to a separate display of needle force. The signal can be calibrated and used to keep the tip 40 of the needle 10 from penetrating structures that require more force than a threshold amount, by having the surgeon S monitor the force sensed by the force sensor 70 and keeping it below the threshold maximum force.

With particular reference to FIG. 7, details of an alternative embodiment needle 110 are described. This alternative needle 110 is configured so that the tip 140 of the needle 110 can act as a distal electrode. The needle 110 includes a shaft 130 extending to the electrode tip 140. Shaft insulation 144 surrounds the shaft 130. Portions of the shaft 130 extending beyond the shaft insulation 144 generally act as an electrode. Preferably the shaft insulation 144 stops just short of the electrode tip 140, so that an approximation of a singular point can be associated with this electrode tip 140. Preferably in this embodiment, a proximal electrode 160 is also provided which is coupled to a wire 162 which preferably has its own insulation jacket 164. Outer insulation 146 can wrap around the wire 162 to hold the wire 162 adjacent to the shaft 130, but while preventing an electrical connection therebetween. The proximal electrode 160 would preferably be provided at a known distance away from the electric tip 140, so that the needle 110 would generally be effective in a manner similar to other multi-electrode needles such as the needle 10 (FIGS. 1-6).

FIG. 9 depicts the embodiment of FIG. 7 in a full sectional end view, according to one embodiment where the wire 162 and insulation jacket 164 are embedded within the outer insulation 146, rather than merely having the outer insulation 46 wrapped outside of the wire 162.

FIG. 8 depicts a unipolar electrode needle 210. This unipolar electrode needle 210 includes a hub 220 with a shaft 230 of the needle 210 extending away from the hub 220 to a tip 240. A proximal electrode 260 is coupled to the shaft 230 a known distance away from the tip 240. A wire 262 extends from the proximal electrode 260 and is fed into the EP mapping system 2 (FIG. 1). Unipolar electrodes such as the proximal electrode 260 function by being coupled with some other electrode within the EP mapping system 2 or associated with some portion of the needle 210, or some other reference, so that meaningful information can be gathered with regard to the position (and preferably also orientation) of the needle 210.

In the embodiment depicted in FIG. 8, the wire 262 is merely wrapped around the exterior of the shaft 230, but could be covered with an outer insulation player, embedded within the shaft 230 or otherwise conveniently routed, or wiring could be dispensed with should be unipolar electrode 260 be fitted with a micro-mechanical power source of some form and a transmitter and other electronics to allow it to function as an electrode without an associated wire 262.

Figure 10:
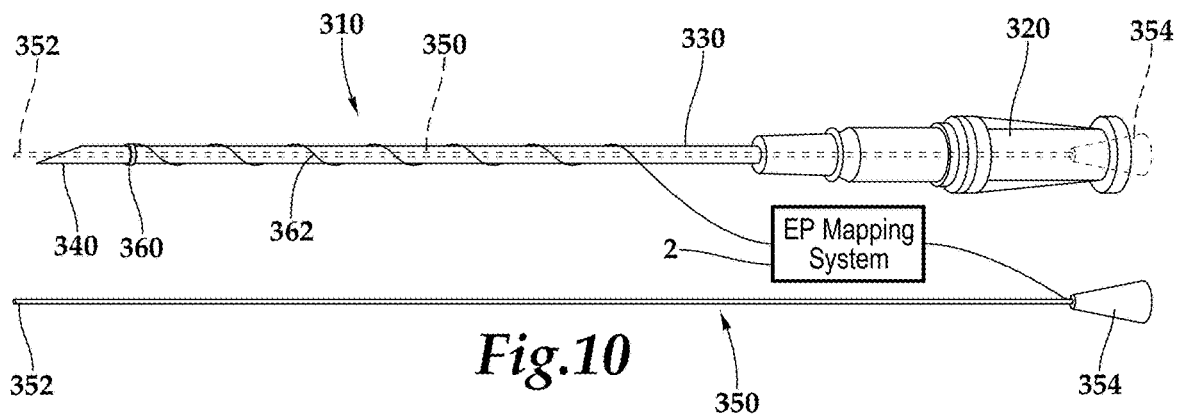
FIG. 10 is a perspective view of an embodiment of that which is shown in FIG. 3 where a single electrode is placed upon the needle and a stylet electrode is associated with the needle, the stylet electrode shown exterior to the needle and shown in broken lines placed within the needle, the pericardiocentesis needle modifiable in form and size to be a percutaneous luminal access needle.

With particular reference to FIG. 10, details of a needle/stylet 310 combination are described. In this embodiment a hub 320 supports a shaft 330 extending out to a tip 340, similar to the needle 10 depicted in FIG. 3. However, only one electrode in the form of a proximal electrode 360 is provided on this shaft 330 spaced a known distance away from the tip 340. Wire 362 preferably extends from this proximal electrode 360 and is fed to the EP mapping system 2. A stylet 350 is also coupled to the EP mapping system 2 and has a distal end 352 opposite a base 354. The stylet 350 is preferably sufficiently long that the distal end 352 of the stylet 350 can pass entirely through a hollow center of the shaft 330 and extend out of the tip 340. The stylet 350 is preferably formed of electrically conductive material so that the distal end 352 can act as an electrode in this embodiment. As an alternative (or in addition), one or more magnetic field sensors can be placed on the stylet to convey its position (and preferably also orientation within the EP mapping system 2).

Preferably the shaft 330 is formed of electrically non-conductive material. As an alternative, the stylet 350 can have an outer insulative jacket formed of electrically non-conductive material or an interior of the shaft 330 can be coated with or otherwise lined with electrically non-conductive material. Between the distal end 352 of the stylet 350 and the proximal electrode 360, the combined needle/stylet 310 can function similar to a dual electrode needle such as that disclosed in FIGS. 1-6. The stylet 350 is movable relative to the shaft 330. The distal end 352 of the stylet 350 can be provided as a blunt tip, or with a sharpened tip, and with the tip 340 of the shaft 330 configured either to be sharp or somewhat blunted, so the various different functionalities can be provided between the shaft 330 and stylet 350 as is known in the stylet and needle arts as they pertain to cardiac surgery and related medical procedures and devices.

Figure 11:
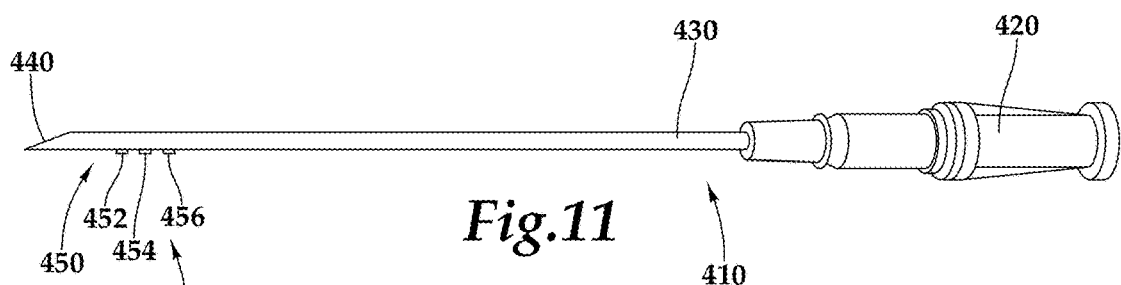
FIG. 11 is a perspective view of an embodiment of that which is shown in FIG. 3 which utilizes magnetic field sensors rather than electrodes, such as for use within the EP mapping system of FIG. 2, the pericardiocentesis needle modifiable in form and size to be a percutaneous luminal access needle.

With particular reference to FIG. 11, a needle 410 is disclosed which includes sensors which are preferably in the form of a magnetic field sensor set 450. The needle 410 includes a hub 420 upon which a shaft 430 is supported and extending out to a tip 440. The magnetic field sensor set 450 preferably includes three separate magnetic field sensors 452, 454, 456, such as sensors oriented in three mutually perpendicular orientations (e.g. X, Y and Z axes), so that the magnetic field from the sources 9 (FIG. 2) can be most accurately characterized at the location adjacent to this magnetic field sensor set 450. For simplicity, the sensors 452, 454, 456 are identified as boxes along a line, but could be oriented non-linearly and would most typically be solenoids or other coils with a generally cylindrical form.

Position (and preferably also orientation) can be ascertained based on a sensed intensity of the magnetic field relative to sources 9 (FIG. 2) of the magnetic field, and the position of bodily structures, and particularly cardiac structures which can be identified by electrodes, other magnetic sensors, other imaging systems, or combinations thereof. Thus, a position of the needle 410 fitted with the magnetic field sensor set 450 can be accurately determined and then displayed on the display 8 of the EP mapping system 2 (FIG. 2).

Figure 12:
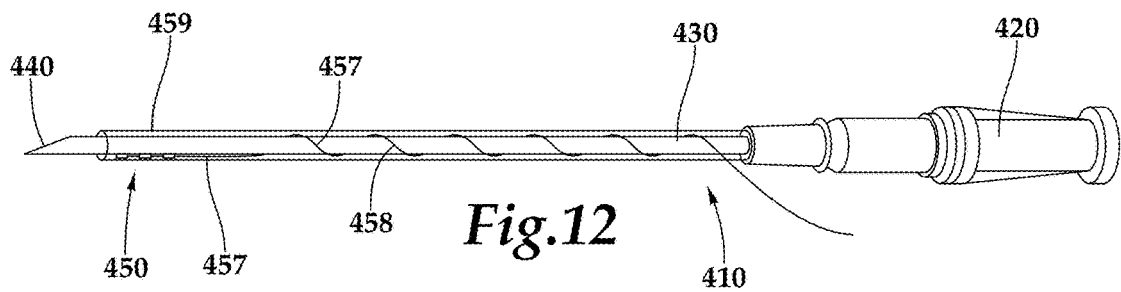
FIG. 12 is a perspective view of a modified version of that which is shown in FIG. 11.

Other details of the needle 410 are preferably similar to those disclosed above with respect to FIGS. 1 and 3-5. In this embodiment, for simplicity, no wires are shown, but typically, and as depicted in FIG. 12, the sensor set 450 would have at least one wire 457 extending therefrom (and optionally three wires in some embodiments) one to each individual sensor 452, 454, 456, and preferably with an insulation jacket 458 outboard of the wire 457 and within a jacket 459 surrounding the wires 457 and holding them adjacent to the shaft 430 of the needle 410, as depicted in FIG. 12, as one example.

Figure 13:
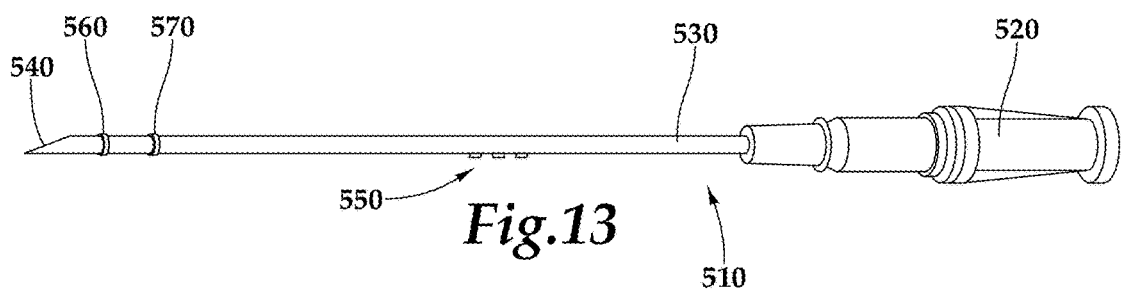
FIG. 13 is a perspective view of an alternative embodiment of that which is shown in FIG. 11 where the magnetic field sensors are located more proximal to a hub of the needle, and with optional electrodes are added to the needle so that a hybrid collection of magnetic field sensors and electrodes are provided together on a common needle, according to this embodiment, the pericardiocentesis needle modifiable in form and size to be a percutaneous luminal access needle.

With particular reference to FIG. 13, a hybrid needle 510 is disclosed that utilizes both magnetic field sensors 550 and at least one electrode 560, 570. In the embodiment depicted, a needle 510 includes a hub 520 with a shaft 530 extending therefrom to a tip 540. The shaft 530, includes a sensor, typically at any location thereon, but in the example depicted slightly closer to the hub 20 than to the tip 540, in the form of a magnetic field sensor set 550. Additionally, at least one electrode, and preferably both a distal electrode 560 and a proximal electrode 570 are also located upon the shaft 530. While wires are not depicted, they would typically extend from these sensors in the form of the magnetic field sensor set 550, as well as from the electrodes 560, 570. Information from the sensors is passed on to the EP mapping system 2 for most accurate visualization of the needle 510.

Figure 14:
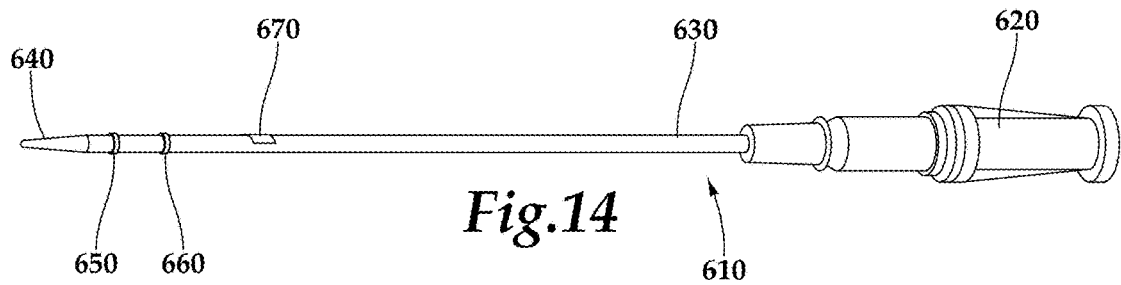
FIG. 14 is a perspective view of a dilator with electrodes thereon for visualization within an EP mapping system such as that disclosed in FIG. 1.

With particular reference to FIG. 14, an embodiment of this invention is depicted where a dilator 610 is fitted with electrodes 650, 660 as one form of sensor to allow for visualization of the dilator 610 within an EP mapping system 2. The dilator 610 includes a hub 620 with a shaft 630 extending therefrom to a tip 640. In this disclosed embodiment, two electrodes 650, 660 are coupled to the shaft 630 at known distances away from the tip 640. A force sensor 670 can also be provided. As one option, one of these electrodes 650 could be located at the tip 640. Typically wires extend from these electrodes 650, 660 and force sensor 670 and appropriate insulation is provided to keep these wires extending from the electrode 650, 660 from shorting out each other as they are routed back to the EP mapping system 2. With such a dilator 610, dilator placement can be most effectively controlled utilizing the EP mapping system 2, and particularly the display 8 thereof, to guide a surgeon S or other medical professional in the placing of the dilator 610 where desired.

With particular reference to FIGS. 15 and 16, two variations on a sheath, including a straight sheath 710 and a curved sheath 810 are disclosed. Shafts 730, 830 are either straight or curved, extending out to tips 740, 840. Hubs 720, 820 are provided opposite these tips 740, 840. With these sheaths 710, 810 valves 725, 825 are preferably provided at the hubs 720, 820 for placement of a dilator or other structure therethrough during a placement (also known as "introduction") procedure. Such devices are also referred to as introducers. A separate fluid control line typically interfaces with the hubs 720, 820, in the form of fluid manifolds 727, 827 to allow for fluid flow after placement of the sheaths 710, 810 where desired. Sensors, depicted in these embodiments as magnetic field sensor sets 750, 850 are provided upon the shafts 730, 830, and preferably adjacent to the tips 740, 840, which allow for a location of these sheaths, and particularly tips thereof, to be visualized through a display 8 of an EP mapping system 2 and for placement where desired. In addition to sheaths 710, 810 other medical devices can similarly be fitted with sensors to facilitate their viewing on a display 8 of an EP mapping system 2. Such other devices include catheters, scalpels, ablation tools, biopsy needles, shunts, drain tubes, etc.

In a simplest form, the pericardiocentesis needle is merely modified to have the needle thereof have a structural size, shape and other characteristics matching those most desirable for percutaneous and other luminal access needles. Other details of the percutaneous needle can be appropriately modified or follow details of the pericardiocentesis needle disclosed above. As described in detail below, after first imaging a luminal access site utilizing the system 1000 of this invention, and as disclosed below, such an appropriately modified needle 10 relating to that disclosed above would be utilized, preferably along with the EP mapping system 1320 (FIG. 24) to gain vascular access. After vascular access has been achieved, appropriate placement of catheters, sheaths, J wires, and other equipment known in the art would occur in preparation for performing of a cardiac procedure or other intravascular procedure.

With particular reference to FIGS. 18-20, the particular details of the system 1000 of this invention are described according to a first embodiment. The system 1000 includes both the probe 1020 and the adapter 1030. The intracardiac ultrasound probe 1020 is a preferred form of imaging tool for use according to this invention. It is understood that other imaging tools could alternatively be utilized including fluoroscopy tools, optical imaging tools, and other imaging tools known in the prior art or developed in the future. Thus, while details of the intracardiac ultrasound probe 1020 are most particularly described, it is recognized that other imaging tools could be utilized, with appropriate modifications as necessary, as an alternative within the scope of this invention.

The probe 1020 includes the tip 1022 at an end of a trunk 1024. The trunk 1024 is of an elongate flexible form and provides an outer enclosure containing wiring and/or other conduits and/or lines in support of equipment adjacent to the tip 1022 for operation of the probe 1020. This trunk 1024 acts as a form of line which contains these pathways, which would most typically include a power supply to an ultrasound emission source, such as a piezo electric crystal or other piezo source 1025 or other ultrasound emitter, and a sensor line for transmitting of a sensed signal from an ultrasound sensor 1028 adjacent to the tip 1022. Preferably the tip 1022 and the trunk 1024 have a similar diameter, with the tip 1022 tapering down to a smaller width as it extends distally. The tip 1022 is preferably relatively blunt, but could include contours to facilitate intraluminal navigation thereof.

The probe 1020 could merely be held at an appropriate position supracutaneously for use of the probe 1020 for visualization of a luminal access site before accessing the appropriate body lumen transcutaneously. However, this is not entirely advantageous in that the probe 1020 is not easily handled in the typically gloved hands of an operator, due to its small size, as well as it smooth cylindrical shape. Thus, it is beneficial to provide an adapter 1032 in large hand grippable shape at this distal end of the probe 1020, which can more readily and easily be held and positioned precisely as desired by an operator.

Furthermore, while a patient's skin is sanitized directly adjacent to a vascular access site, supra cutaneous ultrasound devices often benefit from intimate contact with the epidermis of the patient, and before and after use have significant potential to come into contact with various different structures and surfaces (as well as surrounding air) which can make the probe 1020 less sanitary than desired for placement intravascularly, such as within intracardiac structures. By placement of the adapter 1030 over the probe 1020, the probe 1020 can be pre-sterilized and encapsulated within the adapter 1030, so that the probe 1020 is caused to maintain a sanitary state even when first used with the adapter 1030 in place. When the adapter 1030 is removed, the highly sanitary probe 1020 can then be inserted at the luminal access site into the vasculature of the patient with maximal sanitary conditions being maintained.

To achieve the above objectives, the adapter 1030 could have a variety of different shapes and sizes. Most basic features of a typical adapter 1030 would include a body 1040 which is sized to be of a generally hand grippable size, such as having dimensions in the 1 to 4 inch range for a height, depth and thickness thereof. Typically, a thickness will be less than the other dimensions, and typically length will be greater than other dimensions thereof. The probe 1020 being elongate, typically extends into the body 1040 from an outer portion of into a blind bore 1048 interior cavity. The blind bore 1048 could have a variety of different shapes and sizes, but most preferably has a size and shape closely matching that of the probe 1020 so that the probe 1020 fits snugly within in the blind bore 1048 when placed therein.

Other surfaces of the body 1040 general include a face 1042, which presents a surface which is typically of primary use in placement adjacent to skin of the patient for use of the probe 1020 through the adapter 1030 supracutaneously. This body 1040 also typically includes ends 1044 at opposite portions of the body 1040 which define a length of the body 1040 and sides 1046 which are typically parallel and opposite each other and extend between the ends 1044 and define a width and/or thickness of the adapter 1030.

An echogenic window 1050 or other opening preferably passes through the body 1040 at the face 1042 of the body 1040 and a location and with a shape on the face 1042 adjacent to the piezo source 1026 of the probe 1020, when the probe 1020 is inserted into the blind bore 1048 or other opening into the interior of the body 1040. This window 1050 thus provides a location through which ultrasonic radiation can be emitted and reflected ultrasound waves can return to be picked up by the sensor 1028. In one embodiment, the entire body 1040 could be formed of materials which are at least partially able to transmit ultrasonic waves therethrough, so that the window 1040 could be modified or eliminated.

An interface 1060 defines a portion of the adapter 1030 through which the probe 1020 accesses the blind bore 1048 or other interior space and facilitates attachment of the adapter 1030 to the probe 1020. While the probe 1020 could merely have a friction fit or be placed without attachment into the adapter 1030, most preferably secure attachment is provided between the adapter 1030 and the probe 1020, preferably at the location of the interface 1060. In FIGS. 18 and 19 the interface 1060 is merely configured as a friction fit junction. This interface 1060 could merely be a collar with an aperture diameter slightly less than the diameter of the probe 1020, and formed of a slightly resilient material, so that it can flex to a larger diameter to allow the probe 1020 to pass therethrough, and resiliently exhibits a force holding the probe 1020 therein.

An alternate interface 1070 is depicted in FIG. 3. This alternate interface 1070 features a collar 1072 extending from body 1040 of the adapter 1030. The collar 1072 extends from the base 1074 to a tip 1076. Male threads 1078 extend helically on an outer surface of the collar 1072, preferably from the base 1074 to the tip 1076. The collar 1072 could be of cylindrical form or could exhibit a slight conical taper with the base 1074 larger in diameter than the tip 1076.

A nut 1080 is configured to attach to the collar 1072. The nut 1080 preferably includes a conical bore 1082 passing through an interview thereof from the first end 1084 to a second end 1086. An outer surface 1085 can be gripped by user and rotated (along arrow B of FIG. 3) after the probe 1020 has been inserted into the blind bore 1042 or other interior space (along arrow A of FIG. 3). Female threads 1088 within the conical bore 1082 of the nut 1080 engage with male threads 1078 on the collar 1072 for tightening of the nut 1080 to the collar 1072 of the alternate interface 1070.

By making the nut 1080 have a conical bore 1082 rather than a purely cylindrical bore, as the nut 1080 is tightened, it tends to exhibit interference. The collar 1072 is preferably formed of a resilient material, or as an alternative, the nut 1080 can be formed of a resilient material, or both the collar 1072 and nut 1080 can be formed of a resilient material. Thus, when interference is encountered, further tightening can occur somewhat. Also, the collar 1072 can collapse inwardly radially somewhat under forces applied by rotation of the nut 1080 (along arrow B), causing the collar 1072 to be narrowed in diameter (along arrow C of FIG. 3) and to tighten the collar 1072 down onto the trunk 1024 of the probe 1020 to securely hold the probe 1020 within the body 1040 of the adapter 1030. Other forms of fasteners could be utilized to secure the adapter 1030 to the probe 1020, with such securing being in a removable fashion.

While the adapter 1030 could be used alone upon the probe 1020 to keep the tip 1022 of the probe 1020 covered, most preferably a sleeve 1065 or other sanitary envelope is coupled to the adapter 1030 to cover and keep sanitary the trunk 1024 of the probe 1020 along at least a portion of the trunk 1024 adjacent to the tip 1022. As an example, 1 m of the length of the trunk 1024 could be covered by such a thin plastic sleeve which is non-foraminous and can be coupled to the interface 1060 or otherwise attached to the adapter 1030. In this way, the trunk 1024 would remain covered when the probe 1020 is used supracutaneously. When the adapter 1030 is removed, the sleeve 1065 will correspondingly also be removed, leaving the probe 1020 along with the associated trunk 1024 sanitary and ready for use intravascularly.

Figure 28:
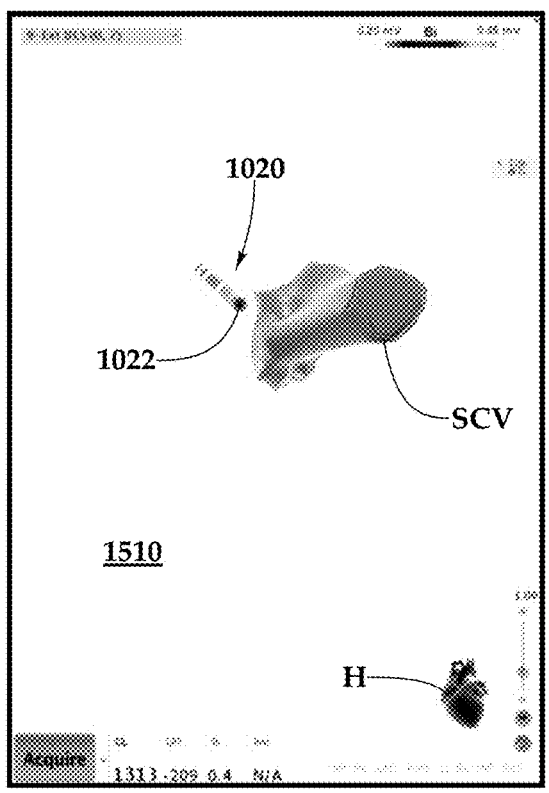
FIG. 28 is an image depicting one visualization facilitated by the intracardiac ultrasound probe and the EP mapping system according to one embodiment of this invention.
Figure 29:
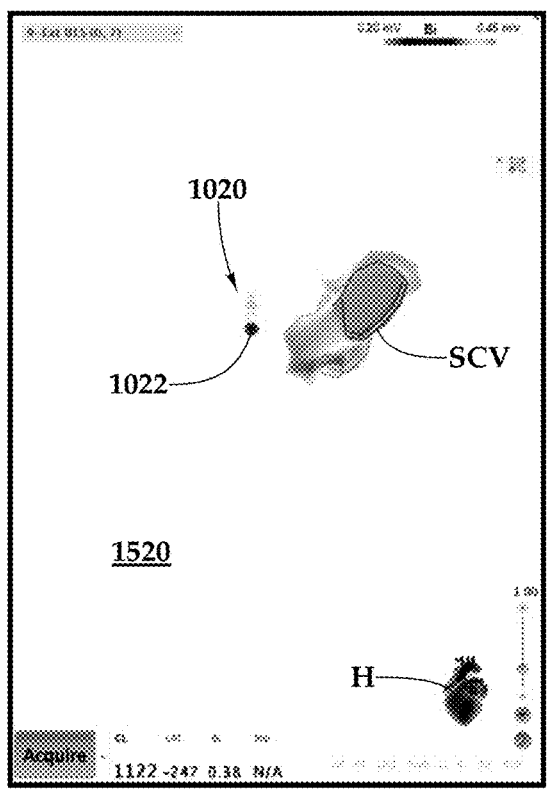
FIGS. 29-32 are images depicting further visualizations facilitated by the intracardiac ultrasound probe and the EP mapping system according to one embodiment of this invention.

The inventor has performed experiments to validate the effectiveness of utilizing intracardiac ultrasound probes supracutaneously at a luminal access site to acquire images both within standard ultrasound imaging displays and imaging within an EP mapping system 1320, and upon the EP mapping display 1330. With particular reference to FIGS. 28-32, actual images obtained by the inventor during various experiments are included herein. In FIG. 28 a subclavian vein SCV is imaged within image 1510. This image shows an orientation of the heart H to help identify the perspective with which the subclavian vein SCV is being imaged. The probe 1020 itself and tip 1022 thereof is also imaged, with this imaging obtained with the probe 1020 located supracutaneously. In FIG. 29 a related image 1520 is provided with the heart H in a slightly different orientation and with the subclavian vein SCV oriented slightly differently, and with the probe 1020 and associated tip 22 all visualized and oriented to provide the best view possible, such as before luminal access transcutaneously to the subclavian vein SCV.

Figure 30:
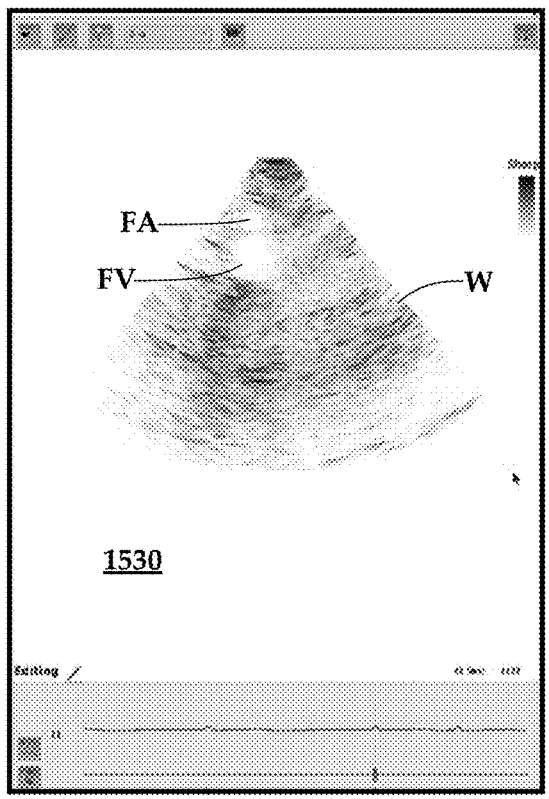
Figure 31:
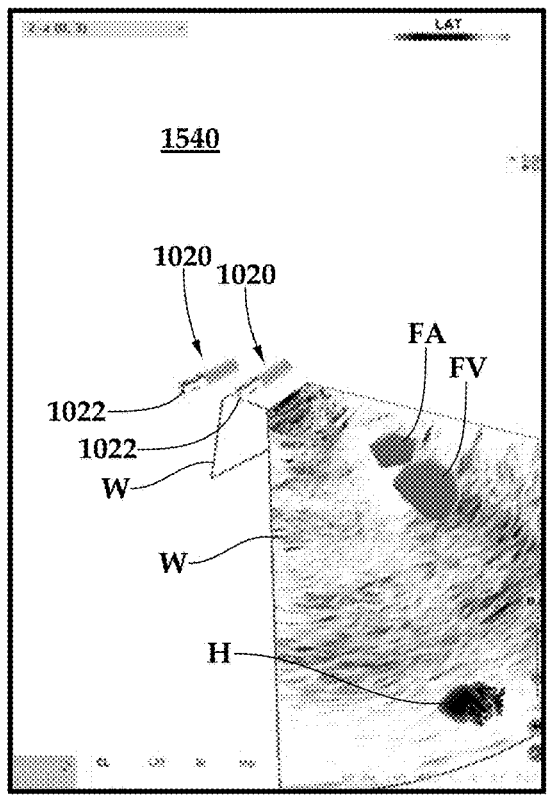
Figure 32:
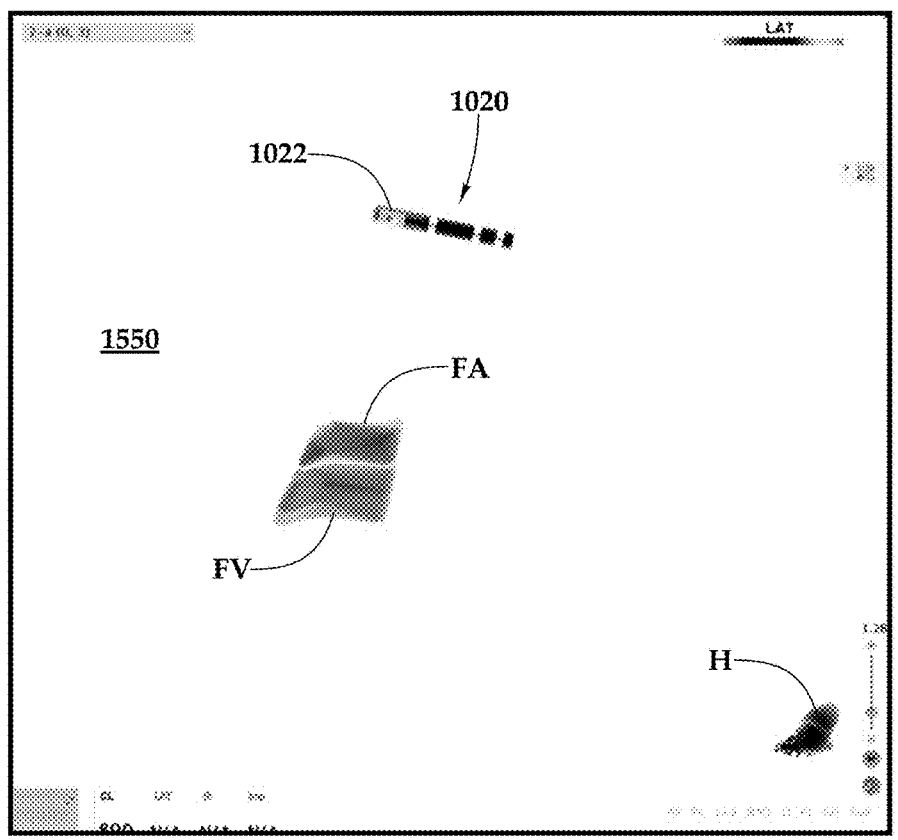

FIGS. 30 and 31 show corresponding utilization of an intracardiac ultrasound probe 1020 coupled to a standard ultrasound display to provide images 1530 (FIG. 30) and 1540 (FIG. 31). An ultrasound window W is depicted and within this window W can be seen the femoral artery FA and the femoral vein FV. Also, within image 1540 (FIG. 31) the orientation of a probe 1020 and tip 1022 are shown for a series of static images along a length of the femoral artery FA and femoral vein FV. These images could be provided on a separate ultrasound display or could be displayed on the display 1330 of an EP mapping system 1310 (FIG. 29).

Figure 24:
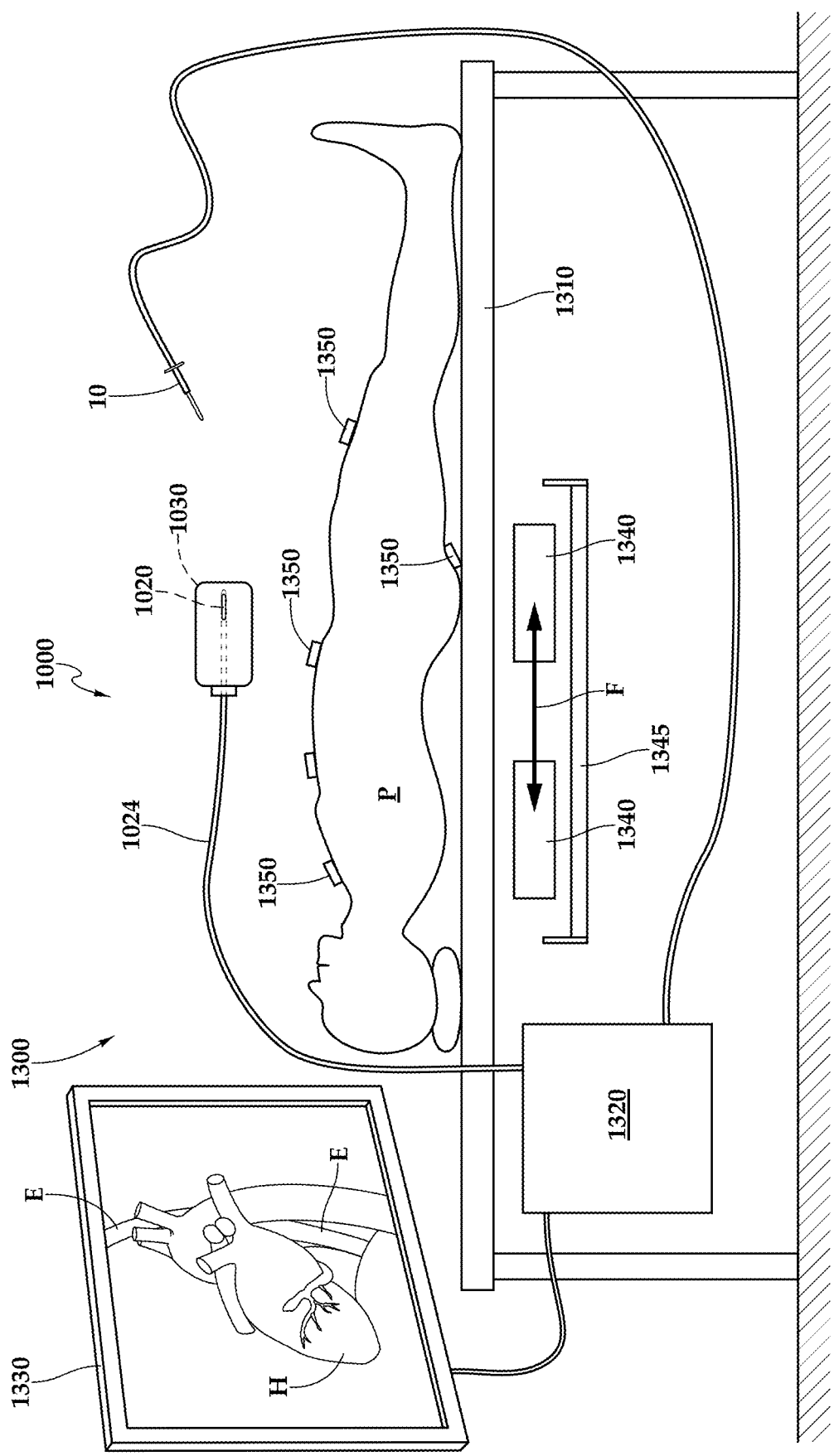
FIG. 24 is a front elevation view of an electrophysiology suite including an electrophysiology mapping system integrated into a table upon which a patient can rest while procedures are performed, and with the EP mapping system modified to include an intracardiac ultrasound probe including a handheld adapter according to this invention, and also with a percutaneous vascular access needle coupled to the EP mapping system, and with the EP mapping system modified to be optimized for visualization both at a luminal access site and at a procedure performance site.

As explained in detail above and with reference to FIGS. 1-16, it is known to provide a pericardiocentesis needle with sensors to allow it to be visualized within an EP mapping system. Such a needle 10 can be appropriately modified to provide luminal access. After having acquired images 1510, 1520, 1530, 1540 (FIGS. 28-32) such a needle 10 can then be utilized and simultaneously visualized within the EP mapping system 1320 on the display 1330 (FIG. 24). The needle 10 can then be guided precisely to the lumen of interest, without having to simultaneously handle the ultrasound probe 1020, which would typically block the most advantageous positions for luminal access with such a needle 10, and would be more cumbersome of a procedure to perform. The probe 1020 and associated adapter 1030 would be on standby and able to be reused if needed, such as if fresh images are required, until adequate access of the appropriate vasculature has been achieved.

Typical intravascular (including intracardiac), procedures are then followed through the vascular access site in preparation for performing an intravascular and/or intracardiac procedure. In many instances, such procedures include visualization with an intracardiac (or other intravascular) ultrasound probe 1020. Rather than having to provide a separate probe 1020 integrated into the EP mapping system 1320, the probe 1020 merely has its adapter 1030 removed, along with any protective sleeve 1065. The probe 1020 can then be inserted at the luminal access site into the appropriate vasculature and routed to a desired imaging location adjacent to where the intracardiac (or other intravascular) procedure is to be performed. This procedure is then performed as noted in the prior art.

With particular reference to FIGS. 22 and 23 a second alternative adopter 1120 is disclosed. With the second alternative adapter 1120, rather than providing an adapter 1030 with a generally orthorhombic shaped case, a more irregular shape is provided for a body 1130 associated with the second adapter 1120. This body 1130 includes a wing 1132 extending laterally from a spine 1134. A head 1136 defines a distal end of the body 1130 which is accessed through a blind bore 1138 into which the tip 1022 of the probe 1020 can be inserted. Clasps 1140 extend down from the spine 1134. Each clasp 1140 preferably includes a pair of facing structures which together define a cylindrical surface 1142 bisected by a slit 1144. The trunk 1024 of the probe 1020 can either snap through the slits 1144 into the clasps 1140 (along arrow D of FIG. 23) or can be passed longitudinally through the clasps 1140 and into the blind bore 1138 (along arrow A of FIG. 22). With the second alternative adapter 1120, the wing 1132 would be utilized in the hand of an operator for guidance of the body 1130. If necessary, an echogenic window can be provided in the head 1136 adjacent to where the tip 1022 and piezo source 1024 of the probe 1020 are located when installed into the second alternative adapter 1120.

Figure 25:
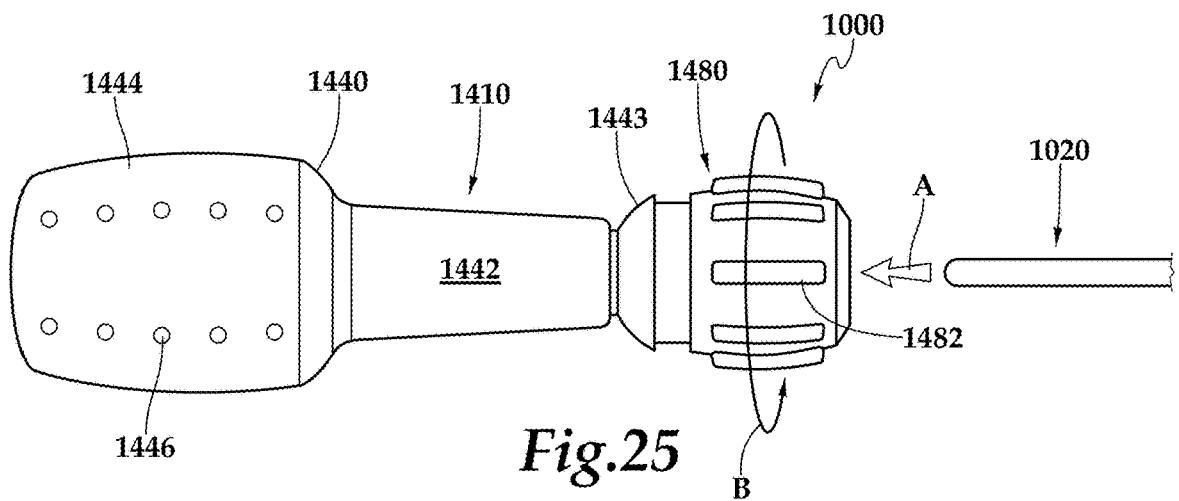
FIG. 25 is an exploded parts view of an intracardiac ultrasound catheter along with a handheld adapter according to a further embodiment of this invention.
Figure 26:
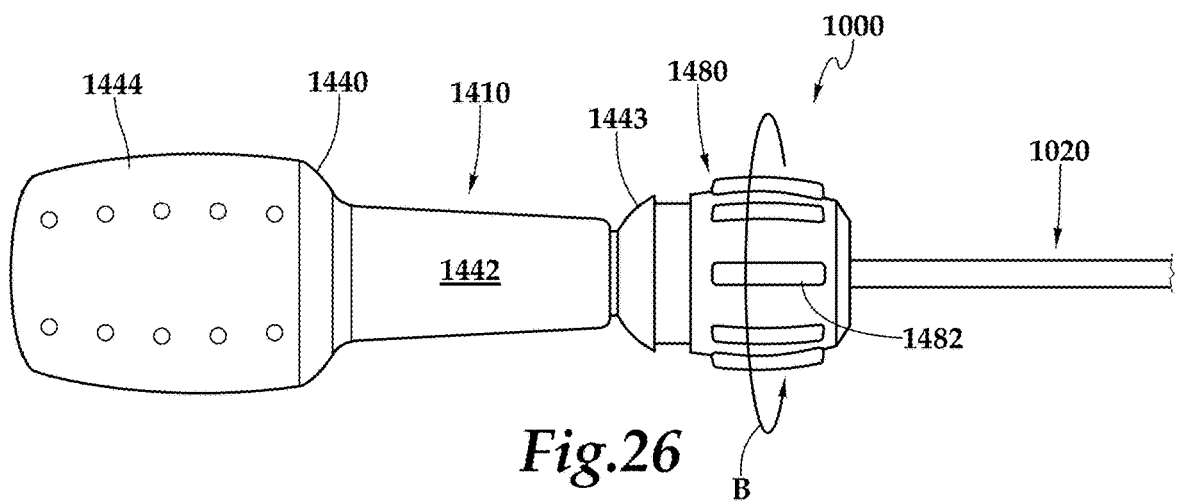
FIG. 26 is a top plan view of that which is shown in FIG. 25, and with the intracardiac ultrasound catheter shown placed into the adapter of FIG. 25.
Figure 27:
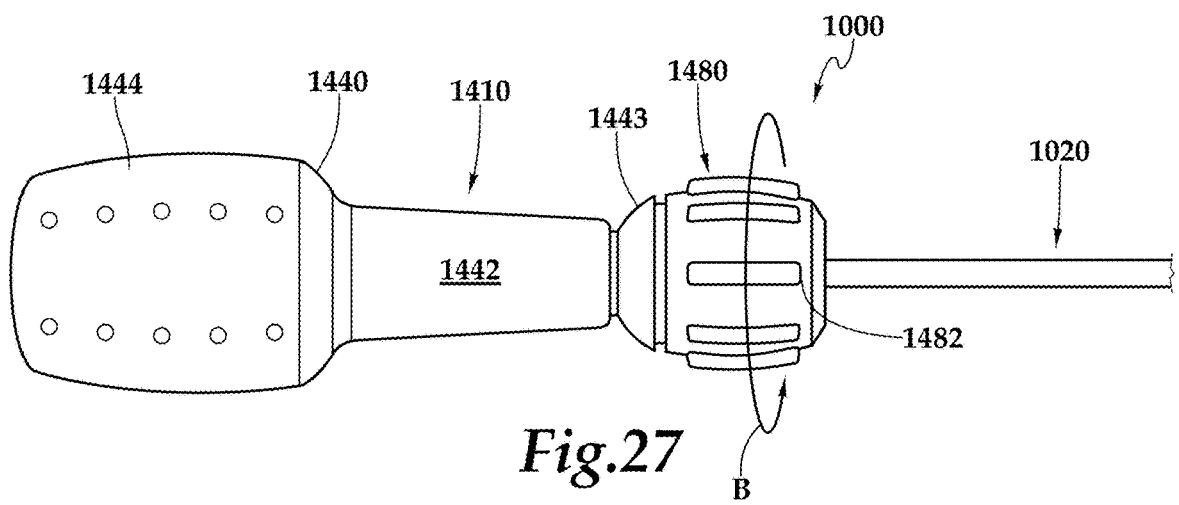
FIG. 27 is a top plan view of that which is shown in FIG. 26, after a nut of an interface of the adapter has been tightened to secure the intracardiac ultrasound catheter to the adapter.

With particular reference to FIGS. 25-27, a third alternative adapter 1410 is described. This third alternative adapter 1410 includes a body 1440 of generally cylindrical form. This form includes a shank 1442 leading to a head MM. Tactile humps 1446 preferably extend from the head 1444 to assist in handling of the head MM. A nut 1480 surrounds the shank 1442 at an interface 1460 located at a support end 1443 of the interface 1460. Ribs 1482 extend from the nut 1480 to assist in gripping and rotating a nut 1480 relative to other portions of the body 1440. The nut 1480 is configured to interact with the support end 1443 so that when the nut 1480 is rotated (along arrow B of FIGS. 8-10) it is caused to tighten down onto the probe 1020 and hold the tip 1022 of the probe 1020 within the head 1444 of the body 1440. Structures within an interior of the nut 1480 could be similar to those associated with the alternate interface 1070 (FIG. 20).

While in a first embodiment it is contemplated that the probe 1020 would be typically an already existing prior art ultrasound probe 1020 configured for use with an EP mapping system 2, 1320 such as those disclose hereinabove, a customized probe 1020 could be provided as an alternative. The probe 1020 can include electrodes and/or magnets and/or magnetic field sensors to assist in precise identifying of a location (and orientation) of the probe 1020 and especially the tip 1022 of the probe 1020, such as within the EP mapping system 1320 (FIG. 24).

Figure 33:
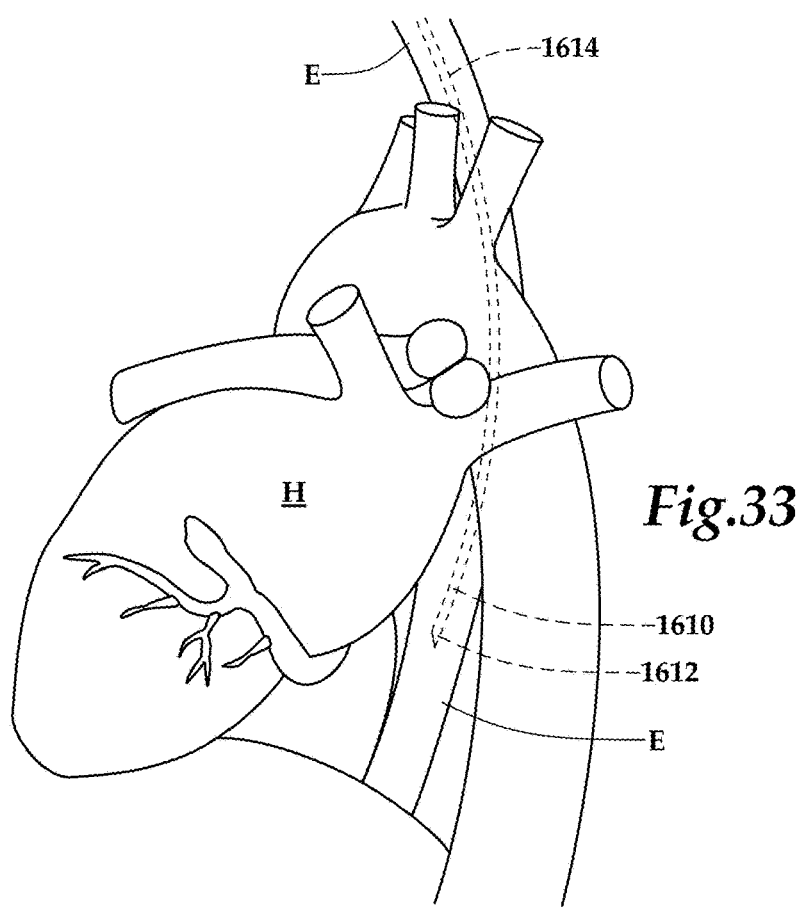
FIG. 33 is an elevation view of a human heart and associated adjacent lumens and depicting positioning of an ultrasound catheter according to one embodiment of this invention, within the esophagus and adjacent to the heart.
Figure 34:
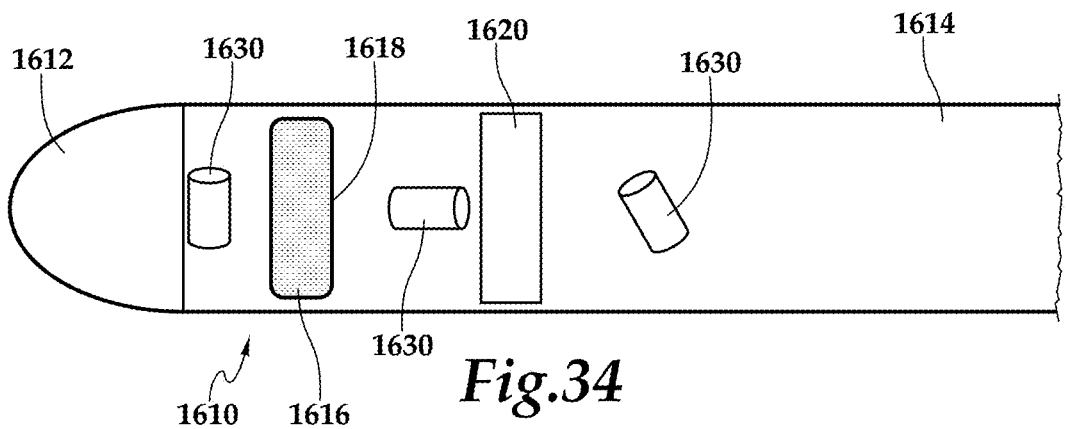
FIG. 34 is a schematic depicting one form of trans-esophageal ultrasound probe which can be integrated into an EP mapping system for visualization, especially adjacent to the heart, according to one embodiment of this invention.
Figure 35:
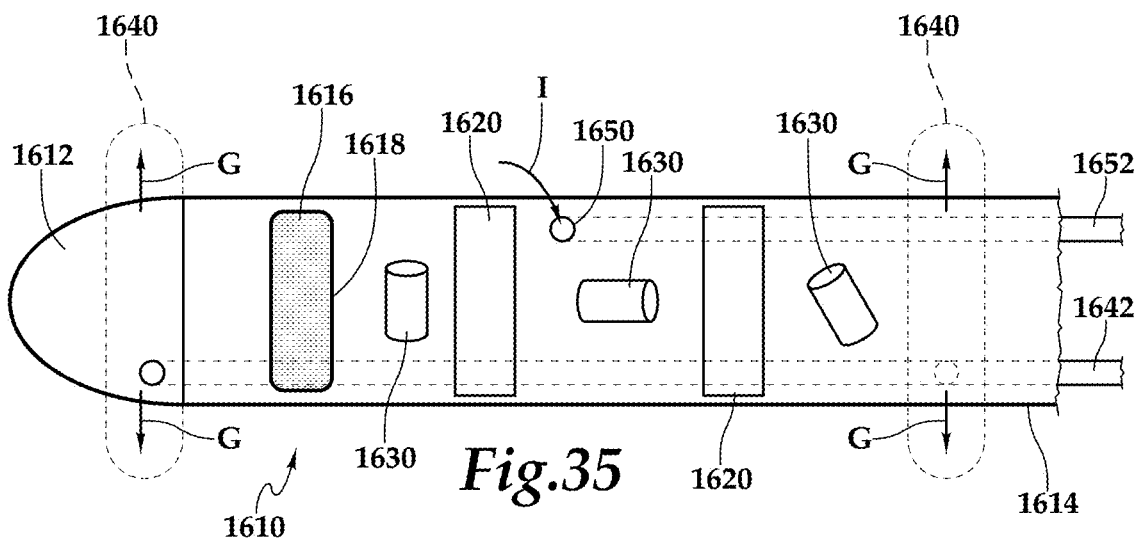
FIG. 35 is a schematic depicting an alternative embodiment trans-esophageal ultrasound probe which can be integrated into an EP mapping system and which optionally includes balloons and/or suction to improve imaging efficacy, especially adjacent to the heart.
Figure 36:
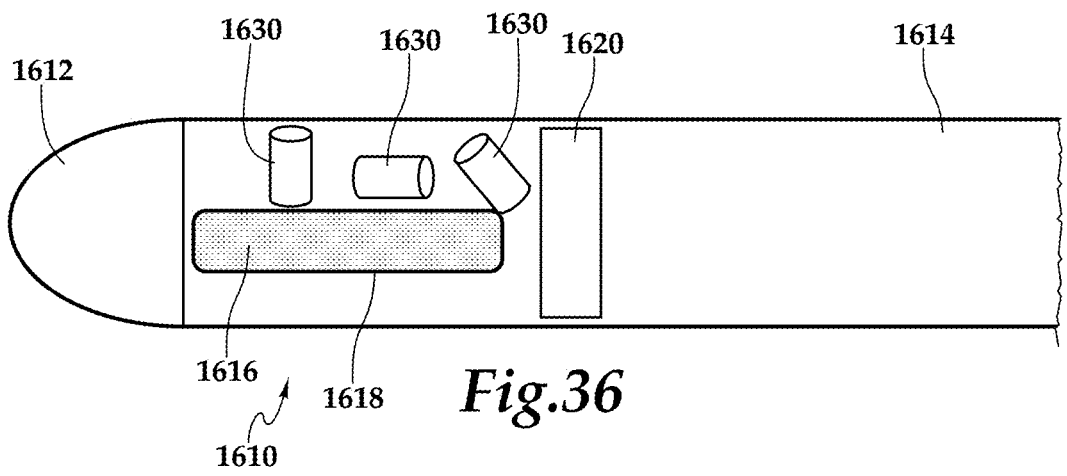
FIG. 36 is a schematic depicting an alternative embodiment trans-esophageal ultrasound probe which can be integrated into an EP mapping system as an alternative embodiment to that which is shown in FIGS. 34 and 35.

Similarly, other probes could be imaged in the EP mapping system 1320 and could be utilized for luminal access or for imaging within various different lumens. With particular reference to FIGS. 34-36 details of a transesophageal echo probe 1610 are described. Such a probe 1610 could be placed transesophageally, such as adjacent to the heart H within the esophagus E (FIG. 33) for ultrasound imaging, such as during an intracardiac procedure.

One particular use of such imaging would be to image various walls of the esophagus E to maintain separation and minimize risk of damage to the esophagus E during heart H procedures such as ablation procedures. Such a probe 1610 when adapted for use within the esophagus E could include a piezo source 1616 which could be lateral to a long axis of the probe 1610 (FIGS. 34 and 35) or parallel with a long axis of the probe 1610 (FIG. 36). The probe 1610 generally includes a tip 1612 at a distal end of a trunk 1614. A sensor 1618 can be provided, typically adjacent to the piezo source 1616, to detect the sonic radiation returning back after reflection off of bodily structures, and which signal associated with the sensor 1618 can be utilized to construct an ultrasound (or other) image (FIGS. 28-32). Such images, rather than being utilized for vascular access, would be utilized to protect the esophagus E and/or to otherwise assist in performing the intracardiac (or other intravascular) procedure.

In one embodiment depicted in FIG. 35, multiple electrodes 1620 are depicted on the probe 1610. The electrodes 1620 are parallel with each other and spaced longitudinally. Furthermore, magnetic field sensors 1630 are provided alone or along with the electrode (or electrodes 1620) such as for imaging within an EP mapping system 1320. In the embodiment depicted in FIG. 35 a balloon 1640 is provided adjacent to the tip 1612, and optionally a second balloon 1640 spaced from the tip 1612. The balloons 1640 can be expanded (along arrow G of FIG. 35), such as through provision of a fluid along a fill line 1642. These two balloons 1640 can be provided on either side of a region of the esophagus E to be protected. A suction port 1650 can be provided in the transesophageal echo probe 1610 between the balloons 1640, which is coupled to a vacuum line 1652 or other source of suction. When activated (drawing fluids along arrow I into the port 1650), walls of the esophagus E could be brought toward the probe 1610 to decrease a diameter of the esophagus E at an area of interest, and move the esophagus E away from the heart H, such as during an ablation procedure and to protect the esophagus E. Simultaneously, the probe 1610 can visualize walls of the esophagus E relative to walls of the heart H, such as to verify that spacing exists and to minimize damage, especially thermal damage to the esophagus E during performing of a cardiac ablation procedure.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When embodiments are referred to as "exemplary" or "preferred" this term is meant to indicate one example of the invention, and does not exclude other possible embodiments. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A method for subcutaneous visualization in support of an intravascular procedure, the method including the steps of:
   first imaging a subcutaneous space at a luminal access site with an imaging tool, the imaging tool having an emission source, an emission sensor and a line coupled to the emissions source with the line extending away from the emission source; the line providing electric power to the emission source and sensor data from the emission sensor; the emission source, the emission sensor and the emission line each sized small enough in width and having sufficient flexibility to navigate through a body lumen;
   accessing a body lumen transcutaneously at the luminal access site with guidance aided by said first imaging step;
   routing the imaging tool through the access site to an intravascular procedure imaging location; and
   second imaging an intravascular procedure location from the intravascular procedure imaging location with the imaging tool.

2. The method of claim 1 wherein after said first imaging step and before said routing step, including the further step of removing an adapter from the imaging tool, said first imaging step occurring with the adapter upon the imaging tool and said second imaging step occurring without the adapter upon the imaging tool; and
   wherein said removing step includes the adapter having an outer wall at least partially surrounding an inner chamber, the inner chamber of the adapter sized to overlie at least a portion of the emission source of the imaging tool and the emission sensor of the imaging tool.

3. The method of claim 2 wherein said first imaging step includes ultrasound waves emissions passing from the ultrasound wave emission source through an echogenic window in the adapter, and with reflected sound waves passing back through the echogenic window for detection by the ultrasound wave sensor.

4. The method of claim 2 wherein said adapter includes an elongate sleeve surrounding said line, said elongate sleeve maintaining a sanitary environment between said elongate sleeve and said line during said first imaging step.

5. The method of claim 2 wherein said removing step includes manipulating a fastener on said adapter, said fastener releasably securing said adapter to a portion of said imaging tool.

6. The method of claim 1 wherein said first imaging step includes the imaging tool emission source including an ultrasound wave emission source, and wherein said emission sensor includes an ultrasound wave sensor.

7. The method of claim 1 including the further step of routing an intravascular procedure tool through the access site of said first imaging step to the intravascular procedure location; and wherein said second imaging step includes the imaging tool moving to the intravascular procedure imaging location separate from the intravascular procedure tool and the imaging tool providing at least one image of the intravascular procedure location.

8. The method of claim 1 wherein said imaging tool of said first imaging step is coupled to an electrophysiology mapping system including a plurality of sensors located upon a patient and a display for displaying subcutaneous spaces, said display providing visualization of the subcutaneous space at the luminal access site of said first imaging step, as well as visualization of the intravascular procedure location during said second imaging step.

9. The method of claim 8 including the further step of moving at least one magnet associated with the EP mapping system from a first position to a second position, the first position placing the at least one magnet closer to the luminal access site than the second position.

10. The method of claim 1 wherein the luminal access site of said first imaging step includes the subcutaneous space adjacent to the femoral artery and/or femoral vein.

11. The method of claim 1 wherein the intravascular procedure location includes an intravascular coronary structure.

* * * * *